United States Patent
Easter et al.

(10) Patent No.: US 11,722,815 B2
(45) Date of Patent: Aug. 8, 2023

(54) IMPLANTABLE MICROPHONE MANAGEMENT

(71) Applicant: Cochlear Limited, Macquarie University (AU)

(72) Inventors: James Roy Easter, Boulder, CO (US); Maekele Gebrekidan, Boulder, CO (US)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 17/228,173

(22) Filed: Apr. 12, 2021

(65) Prior Publication Data
US 2022/0329935 A1    Oct. 13, 2022

Related U.S. Application Data

(62) Division of application No. 15/629,289, filed on Jun. 21, 2017, now Pat. No. 10,973,626.

(51) Int. Cl.
*H04R 1/42*    (2006.01)
*H04R 25/00*    (2006.01)

(52) U.S. Cl.
CPC ............. *H04R 1/42* (2013.01); *H04R 25/407* (2013.01); *H04R 25/48* (2013.01); *H04R 2225/41* (2013.01); *H04R 2430/01* (2013.01)

(58) Field of Classification Search
CPC ........ H04R 1/42; H04R 25/407; H04R 25/48; H04R 2225/41; H04R 2430/01
See application file for complete search history.

(56) References Cited

U.S. PATENT DOCUMENTS

2011/0178438 A1*   7/2011  Van Gerwen ........ H04R 25/606
                                                  600/587
2018/0368975 A1*  12/2018  Easter ..................... A61F 2/18

* cited by examiner

*Primary Examiner* — Mark Fischer
(74) *Attorney, Agent, or Firm* — Piloff Passino & Cosenza LLP; Martin J. Cosenza

(57) ABSTRACT

A device, including an implantable microphone, including a transducer, and a chamber in which a gas is located such that vibrations originating external to the microphone based on sound are effectively transmitted therethrough, wherein the transducer is in effective vibration communication with the gas, wherein the transducer is configured to convert the vibrations traveling via the gas to an electrical signal, the chamber and the transducer correspond to a microphone system, wherein the chamber corresponds to a front volume of the microphone system, and the transducer includes a back volume corresponding to the back volume of the microphone system, and the implantable microphone is configured to enable pressure adjustment of the front and/or back volume in real time.

14 Claims, 24 Drawing Sheets

IMPLANTABLE MICROPHONE MANAGEMENT

CROSS REFERENCE TO RELATED APPLICATIONS

The present application is a Divisional application of U.S. patent application Ser. No. 15/629,289, filed Jun. 21, 2017, now U.S. Pat. No. 10,973,626, naming James Roy EASTER as an inventor, the entire contents of that application being hereby incorporated by reference herein in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

Another type of hearing prosthesis uses an actuator to mechanically vibrate the ossicular chain, whereby an amplified signal can reach the cochlea. This type of hearing prosthesis can have utility for both conductive losses and sensorineural loss, depending on the level of hearing loss. Still another is a bone conduction device that imparts vibration to skull bones to evoke a bone conduction hearing percept.

SUMMARY

In accordance with an exemplary embodiment, there is device, comprising: an implantable microphone, including: a transducer, and a chamber in which a gas is located such that vibrations originating external to the microphone based on sound are effectively transmitted therethrough, wherein the transducer is in effective vibration communication with the gas, wherein the transducer is configured to convert the vibrations traveling via the gas to an electrical signal, the chamber and the transducer correspond to a microphone system, wherein the chamber corresponds to a front volume of the microphone system, and the transducer includes a back volume corresponding to the back volume of the microphone system, and the implantable microphone is configured to enable pressure adjustment of the front and/or back volume in real time.

In another exemplary embodiment, there is a device, comprising: an implantable microphone, including: a transducer, and a chamber in which a gas is located such that vibrations originating external to the microphone based on sound are effectively transmitted therethrough, wherein the transducer is in effective vibration communication with the gas, wherein the transducer is configured to convert the vibrations traveling via the gas to an output signal, the chamber and the transducer correspond to a microphone system, wherein the chamber corresponds to a front volume of the microphone system, and the transducer includes a back volume corresponding to the back volume of the microphone system, and the implantable microphone is configured to enable a volumetric size change of at least one of the back volume outside of the transducer or the front volume outside the transducer.

In another exemplary embodiment, there is an implantable microphone system; and an implantable noise cancellation system, wherein the hearing prosthesis is configured to evoke a hearing percept based on frequencies above a given frequency captured by the microphone system and adjust the noise cancellation system transfer function to accommodate for changes in an environment of the recipient, and the implantable microphone is configured to adjust a pressure within a microphone volume in a timeframe fast enough that the adjustment accommodates the noise cancellation system and slow enough that the adjustment accommodates the microphone system.

In another exemplary embodiment, there is a method, comprising: capturing at a first temporal location first sound originating external to a recipient with an implanted microphone system implanted in the recipient while the implanted microphone system has a first transfer function; subsequent to the first temporal location, at a second temporal location, experiencing a first event that causes the first transfer function to change to a second transfer function different from the first transfer function; and during a first temporal period beginning after the first temporal location, while continuing to experiencing the first event, automatically changing the transfer function of the microphone system at least back towards the first transfer function via pressure management within the microphone.

BRIEF DESCRIPTION OF THE DRAWINGS

Embodiments of the present invention are described below with reference to the attached drawings, in which.

DETAILED DESCRIPTION

Figure 1:
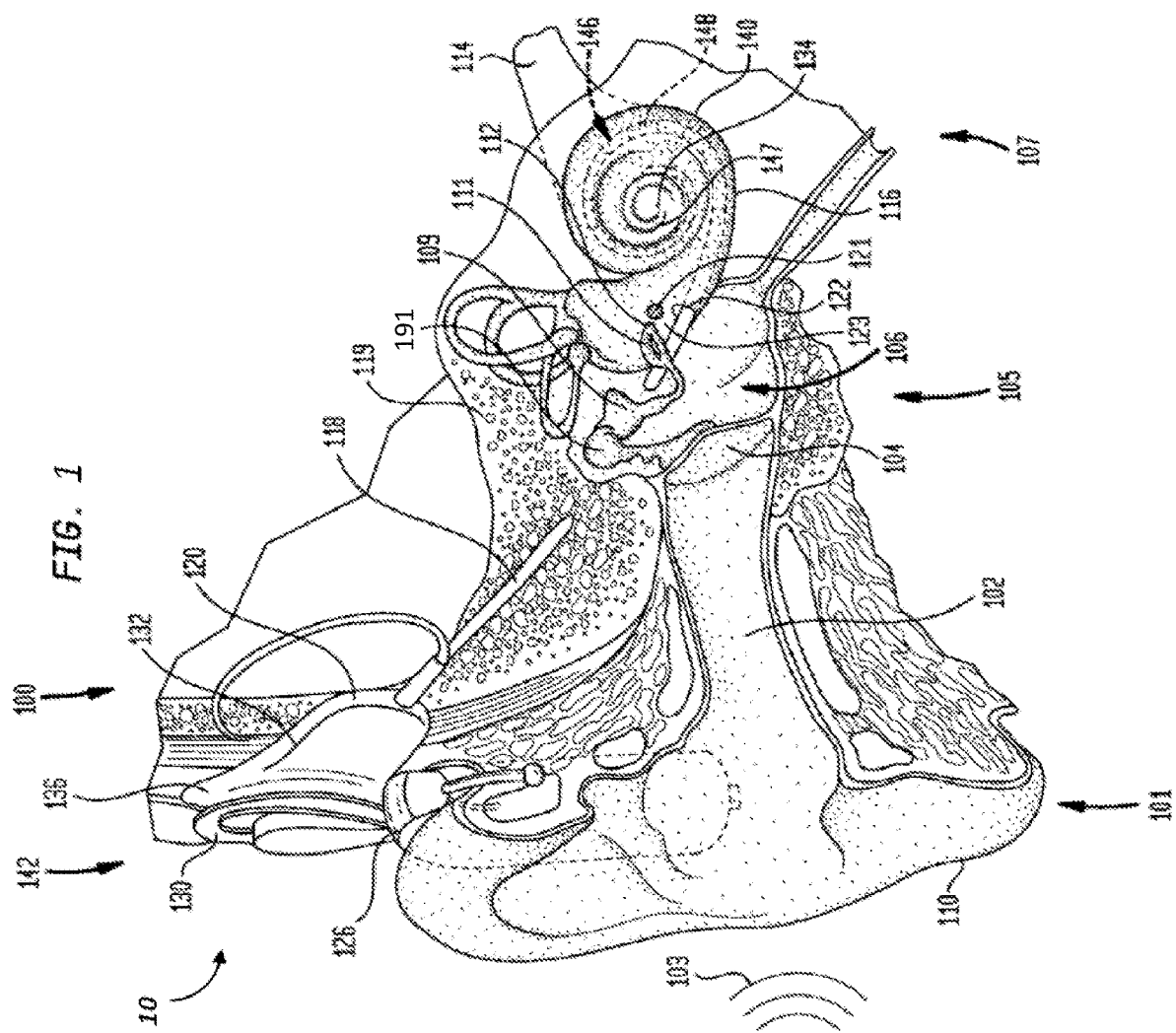
FIG. 1 is a perspective view of an exemplary hearing prosthesis in which at least some of the teachings detailed herein are applicable.

FIG. 1 is perspective view of a totally implantable cochlear implant, referred to as cochlear implant 100, implanted in a recipient, to which some embodiments detailed herein and/or variations thereof are applicable. The totally implantable cochlear implant 100 is part of a system 10 that can include external components, in some embodiments, as will be detailed below. It is noted that the teachings detailed herein are applicable, in at least some embodiments, to any type of hearing prosthesis having an implantable microphone.

It is noted that in alternate embodiments, the teachings detailed herein and/or variations thereof can be applicable to other types of hearing prostheses, such as, for example, bone conduction devices (e.g., active transcutaneous bone conduction devices), Direct Acoustic Cochlear Implant (DACI) etc., middle ear implants, etc. Embodiments can include any type of hearing prosthesis that can utilize the teachings detailed herein and/or variations thereof. It is further noted that in some embodiments, the teachings detailed herein and/or variations thereof can be utilized other types of prostheses beyond hearing prostheses.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 191, the incus 109, and the stapes 111. Bones 191, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is recharged by the power provided from the external device 142. In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown, but details of such an exemplary embodiment are described below) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120).

In at least some embodiments, the teachings detailed herein and/or variations thereof can be utilized with any type of implantable microphone arrangement. Some additional details associated with the implantable microphone assembly 137 will be detailed below.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source can comprise, for example, a rechargeable battery. During operation of cochlear implant 100, the power stored by the power source is distributed to the various other implanted components as needed. The power source may be located in main implantable component 120, or disposed in a separate implanted location.

In some exemplary embodiments, a signal sent to the stimulator of the cochlear implant can be derived from an external microphone as a substitute to the implantable microphone. DACIs, middle ear implants, and bone conduction devices can also use an implanted microphone, and thus are also fully implantable devices, but can alternatively derive a signal from an external microphone as a substitute/alternative. Fully implantable devices can have utility by presenting improved cosmesis, can have an improved immunity to certain noises (e.g., wind noise), can present few opportunities for loss or damage, and can at least sometimes be more resistant to clogging by debris or water, etc.

Implanted microphones can detect pressure in some embodiments. In at least some embodiments, they are configured to detect air pressure which is subsequently transmitted through the tissue to the microphone. Implanted microphones can detect other pressures presented to their surface, which can be undesirable in certain circumstances. One type of pressure which can represent an impairment to the performance of an implanted microphone is pressure due to acceleration. In some embodiments, such acceleration can have a deleterious effect on a hearing prosthesis if it is in the desired operational frequency range of the prosthesis, typically 20 Hz to 20 kHz, although narrower ranges still give satisfactory speech intelligibility. Accelerations may arise from, for example, foot impact during walking, motion of soft tissue relative harder tissues, wear of harder tissues against each other, chewing, and vocalization.

In some embodiments, the accelerations induce pressure on the microphone, which cannot distinguish the desired pressure due to external sounds from the largely undesired pressure due to internal vibration originating directly from the body, or borne to the microphone through the body from an implanted actuator. The accelerations can be thought of as giving rise to these pressures by virtue of the microphone being driven into the tissue. If the microphone is securely mounted on the skull, and the skull vibrates normal to its surface, the microphone diaphragm will be driven into the tissue which, due to the mass, and hence inertia of the tissue, can present a reactive force to the microphone. That reactive force divided by the area of the microphone is the pressure generated by acceleration. The formula for acceleration pressure can be:

$$\Delta P = \rho \cdot t \cdot a$$

where $\Delta P$ is the instantaneous pressure above $P_0$, the ambient pressure, $\rho$ is the mean density of tissue over the microphone, t is the mean thickness of tissue over the microphone, and a is the instantaneous acceleration. When the acceleration is normal but into the surface rather than away from the surface, a decrease in pressure is generated rather than an increase.

In some instances, there can be utilitarian value to reducing signal outputs due to acceleration. Because the relative body-borne to air-borne pressure of an implanted microphone is typically 10-20 dB higher than that that occurs in normal hearing, body originating sounds can be louder relative to externally originating sound. Such large ratios of vibration to acoustic signals are experienced by a recipient as banging and crashing during movement, very noisy chewing, and their own voice being abnormally loud relative to other speakers. At the same time, it should be noted that there is utilitarian value in avoiding the cancellation of all or part of the recipient's own voice. Complete cancellation of the recipient's own voice can result in, in some embodiments, the recipient speaking very loudly compared to other speakers. It is therefore utilitarian to reduce the ratio of vibration to acoustic signals to a level, such as a comparable level, to that found in normal hearing. In some embodiments, this can be achieved by an effective reduction of the acceleration pressure/air-borne pressure sensitivity of 10-20 dB. By doing so, a ratio of acoustic signal to vibration signal similar to what is experienced in normal hearing, and hence a more natural listening experience, can be achieved.

Additionally, signal borne by the body from an actuator as in a DACI or a middle ear implant (in those embodiments) can be amplified by the signal processing of the implant, and can present a gain of greater than 1 at some frequency around the loop formed by the microphone, signal processing, actuator, and tissue. This is can be the case when dealing with high gains such as may be the case with moderate to large hearing loss. Under such circumstances, unless additional steps are taken such as are disclosed herein, the hearing prosthetic system can undergo positive feedback at some frequency and begin "singing," or oscillating. This oscillation can reduce the speech intelligibility, effectively masking out at least the frequency at which oscillation is occurring at, and often other frequencies through a psychoacoustic phenomenon called spread of masking. It can be annoying for the recipient, because the oscillation can occur at a very loud level, and increases the load on the battery, shortening required time between changing or charging batteries. This can require a much greater reduction in feedback of 25-55 dB (often 35-45 dB), and can depend upon the hearing loss of the recipient, as the more hearing loss of the recipient, the more gain will need to be given in the signal processing, at least in some instances.

An exemplary embodiment that includes an implantable microphone assembly utilizes a motion sensor to reduce the effects of noise, including mechanical feedback and biological noise, in an output response of the implantable microphone assembly. In an exemplary embodiment, the diaphragm of the implantable microphone assembly that vibrates as a result of waves traveling through the skin of the recipient originating from an ambient sound, can be also affected by body noise and the like. To actively address non-ambient noise sources (e.g., body noise conducted through tissue of a recipient to a microphone, which in at least some embodiments is not of an energy lever and/or frequency to be audible at a location away from the recipient, at least not without sound enhancement devices) of vibration of the diaphragm of the implantable microphone and thus the resulting undesired movement between the diaphragm and overlying tissue, some embodiments utilize a motion sensor to provide an output response proportional to the vibrational movement experienced by the microphone assembly. Generally, the motion sensor can be mounted anywhere such that it enables the provision of a sufficiently accurate representation of the vibration received by the implantable microphone in general, and the diaphragm of the implantable microphone, in particular. The motion sensor can be part of the assembly that contains the microphone/diaphragm thereof, while in an alternate embodiment it can be located in a separate assembly (e.g. a separate housing etc.). In an exemplary embodiment, the motion sensor is substantially isolated from the receipt of the ambient acoustic signals originating from an ambient sound that pass transcutaneously through the tissue over the microphone/diaphragm of the microphone and which are received by the microphone diaphragm. In this regard, the motion sensor can provide an output response/signal that is indicative of motion (e.g., caused by vibration and/or acceleration), whereas a transducer of the microphone can generate an output response/signal that is indicative of both transcutaneously received acoustic sound and motion. Accordingly, the output response of the motion sensor can be removed from the output response of the microphone to reduce the effects of motion on the implanted hearing system.

Figure 2:
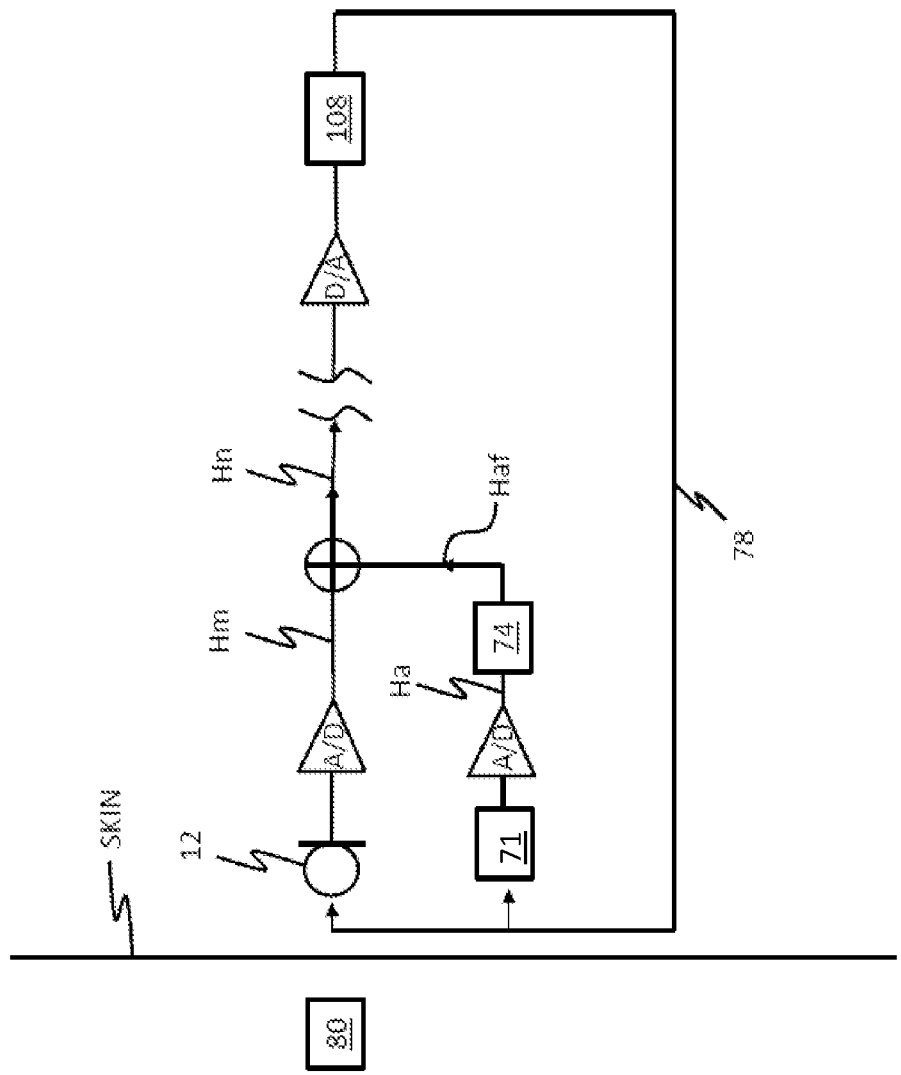
FIG. 2 schematically illustrates an implantable hearing system that incorporates an implantable microphone assembly and motion sensor 71.

Accordingly, to remove noise, including feedback and biological noise, it is utilitarian to measure the acceleration of the microphone assembly. FIG. 2 schematically illustrates an implantable hearing system that incorporates an implantable microphone assembly having a microphone 12 including a diaphragm and motion sensor 71. As shown, the motion sensor 71 further includes a filter 74 that is utilized for matching the output response Ha of the motion sensor 71 to the output response Hm of the microphone 12. Of note, the diaphragm of microphone 12 is subject to desired acoustic signals (i.e., from an ambient source 103), as well as undesired signals from biological sources (e.g., vibration caused by talking, chewing etc.) and, depending on the type of output device 108 (e.g., bone conduction vibratory apparatus, DACI actuator, and, in some instances, cochlear implant electrode array) feedback from the output device 108 received by a tissue feedback loop 78. In contrast, the motion sensor 71 is substantially isolated (which includes totally isolated) from the ambient source and is subjected to only the undesired signals caused by the biological source and/or by feedback received via the feedback loop 78.

Accordingly, the output of the motion sensor 71 corresponds the undesired signal components of the microphone 12. However, the magnitude of the output channels (i.e., the output response Hm of the microphone 12 and output response Ha of the motion sensor 71) can be different and/or shifted in phase. In order to remove the undesired signal components from the microphone output response Hm, the filter 74 and/or the system processor can be operative to filter one or both of the responses to provide scaling, phase shifting and/or frequency shaping. The output responses Hm and Ha of the microphone 12 and motion sensor 71 are then combined by summation unit 76, which generates a net output response Hn that has a reduced response to the undesired signals.

In order to implement a filter 74 for scaling and/or phase shifting the output response Ha of a motion sensor 71 to remove the effects of feedback and/or biological noise from a microphone output response Hm, a system model of the relationship between the output responses of the microphone 12 and motion sensor 71 is identified/developed. That is, the filter 74 can be operative to manipulate the output response Ha of the motion sensor 71 to biological noise and/or feedback, to replicate the output response Hm of the microphone 12 to the same biological noise and/or feedback. In this regard, the filtered output response Haf and Hm may be of substantially the same magnitude and phase prior to combination (e.g., subtraction/cancellation). However, it will be noted that such a filter 74 need not manipulate the output response Ha of the motion sensor 71 to match the microphone output response Hm for all operating conditions. Rather, the filter 74 can match the output responses Ha and Hm over a predetermined set of operating conditions including, for example, a desired frequency range (e.g., an acoustic hearing range) and/or one or more pass bands. Note also that the filter 74 can accommodate the ratio of microphone output response Hm to the motion sensor output response Ha to acceleration, and thus any changes of the feedback path which leave the ratio of the responses to acceleration unaltered have little or no impact on good cancellation. Such an arrangement thus can have significantly reduced sensitivity to the posture, clenching of teeth, etc., of the recipient.

Figure 3A:
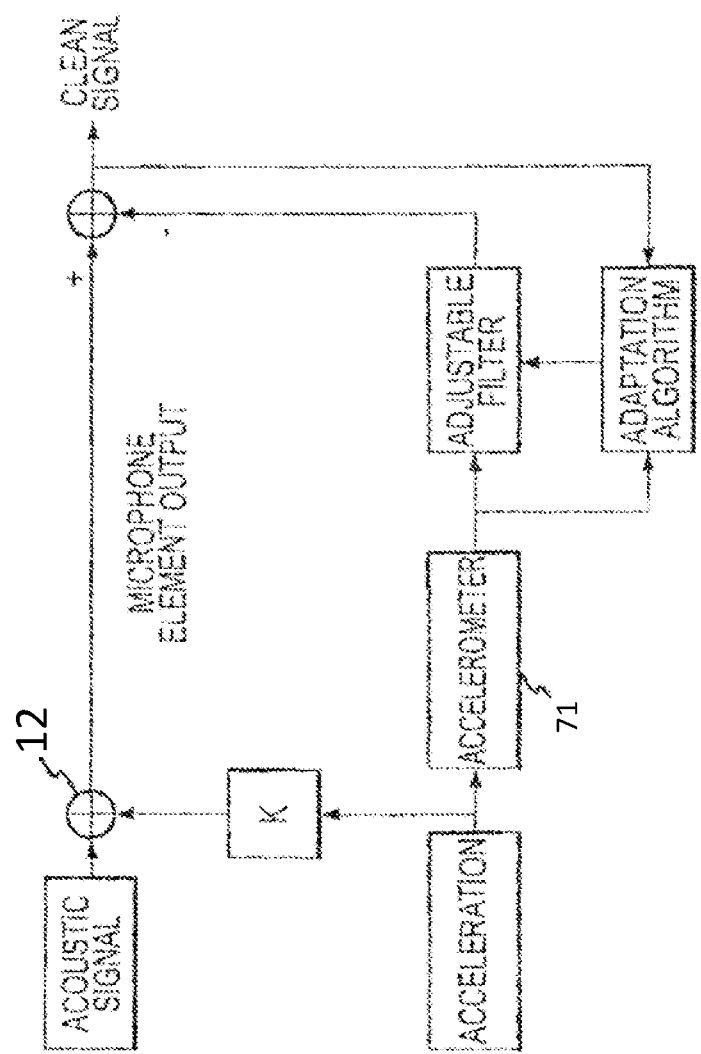
FIG. 3A functionally illustrates an exemplary use of adaptive filters.

An exemplary embodiment utilizes adaptive filter(s) to filter out body noise and the like. More particularly, FIG. 3A functionally illustrates an exemplary use of such adaptive filters. In FIG. 3, biological noise is modeled by the acceleration at the microphone assembly filtered through a linear process K. This signal is added to the acoustic signal at the surface of the microphone element. In this regard, the microphone 12 sums the signals. If the combination of K and the acceleration are known, the combination of the accelerometer output and the adaptive/adjustable filter can be adjusted to be K. This is then subtracted out of the microphone output at point. This will result in the cleansed or net audio signal with a reduced biological noise component. This net signal may then be passed to the signal processor where it can be processed by the hearing system.

Figure 3B:
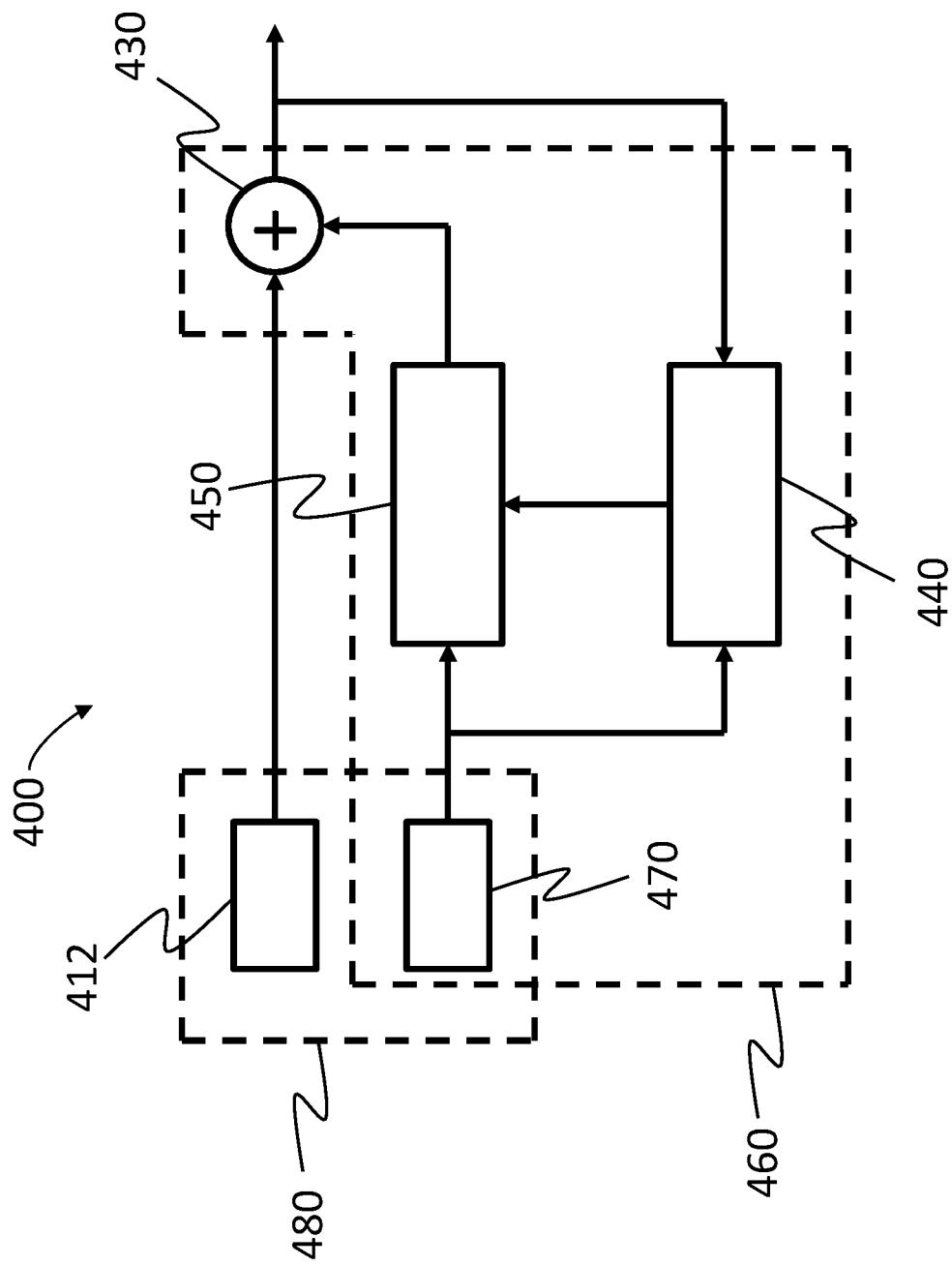
FIG. 3B functionally depicts an exemplary embodiment of a system that is usable in the hearing prosthesis of FIG. 1 that functionally operates in accordance with the schematic of FIG. 3A.

FIG. 3B functionally depicts an exemplary embodiment of a system 400 that is usable in the hearing prosthesis 10 of FIG. 1 that functionally operates in accordance with the schematic of FIG. 3A. As can be seen, the system 400 includes microphone 412 and accelerometer 470. The microphone 412 is configured such that it receives signals resulting from the ambient sound, as well as biological noise/body noise, including, in at least some embodiments, signals resulting from a recipient's own voice that travels through the body via bone conduction/tissue conduction.

These latter signals are added at the microphone 412 to the signals resulting from ambient sound because the microphone 412 detects both signals. Conversely, accelerometer 470 is functionally isolated from the signals resulting from the ambient sound, and generally only responds to body noise signals and/or feedback signals. The system 400 incorporates an adjustable filter apparatus 450 controlled by a control unit 440 that runs an adaptive algorithm to control the filter(s) of the adjustable filter apparatus 450. Details of the adaptive algorithm are provided below, but briefly, as can be seen, the output of the adaptive filter apparatus 450, controlled by filter control unit 440, is fed to adder 430, wherein it is added to (or, more accurately, subtracted from) the output of the microphone 412, and passed on to a signal processor and/or an output device (not shown, but, for example, a receiver stimulator of a cochlear implant, an actuator of a DACI, and/or an actuator (vibrator) of an active transcutaneous bone conduction device) of the hearing prosthesis system 400. Collectively, the accelerometer 470, the adjustable filters 450, the filter control unit 440, and the adder 430 corresponds to an adaptive noise cancellation sub-system 460.

Adaptive filters can perform this process using the ambient signals of the acceleration and the acoustic signal plus the filtered acceleration. The adaptive algorithm and adjustable filter can take on many forms, such as continuous, discrete, finite impulse response (FIR), infinite impulse response (IIR), lattice, systolic arrays, etc. Some exemplary algorithms for the adaptation algorithm include stochastic gradient-based algorithms such as the least-mean-squares (LMS) and recursive algorithms such as RLS. Alternatively and/or in addition to this, algorithms which are numerically more stable can be utilized in some alternate embodiments, such as the QR decomposition with RLS (QRD-RLS), and fast implementations somewhat analogous to the FFT. The adaptive filter can incorporate an observer, that is, a module to determine one or more intended states of the microphone/motion sensor system. The observer can use one or more observed state(s)/variable(s) to determine proper or utilitarian filter coefficients. Converting the observations of the observer to filter coefficients can be performed by a function, look up table, etc. In some exemplary embodiments, adaptation algorithms can be written to operate largely in the digital signal processor "background," freeing needed resources for real-time signal processing.

Figure 4:
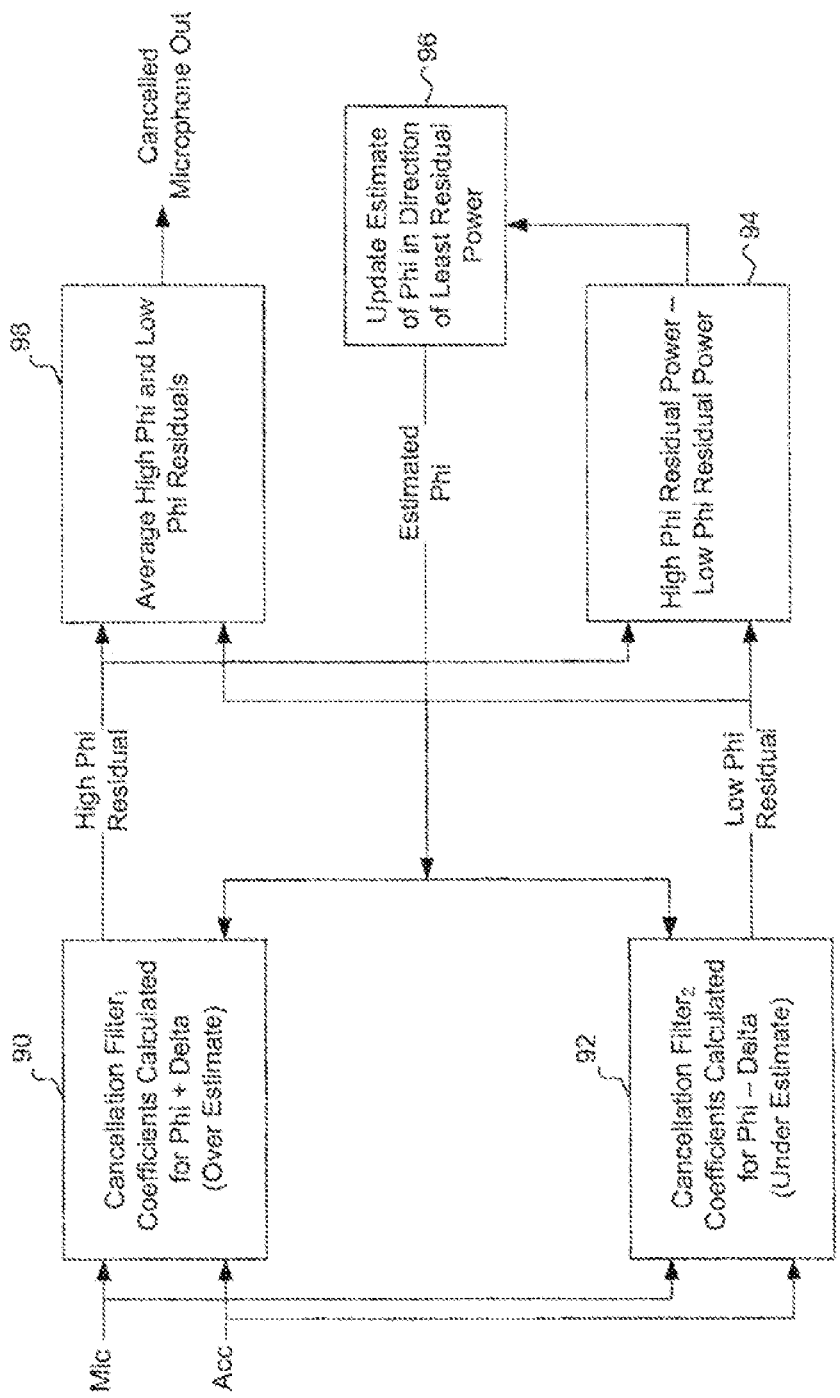
FIG. 4 is a schematic illustration of an embodiment of an implantable hearing prosthesis that utilizes a plurality of cancellation filters.

FIG. 4 presents a functional diagram of an exemplary adaptive filter arrangement that utilizes an adaptive filter that adapts based on current operating conditions (e.g., operating environment) of the implantable hearing prosthesis. It is noted that the teachings detailed herein and/or variations thereof can be combined with some or all of the teachings of U.S. Patent Application Publication No. 2012/0232333, published on Sep. 13, 2012, to Inventor Scott Allan Miller, a co-inventor of this application. In this regard, at least some embodiments include devices, systems and/or methods that utilize one or more or all of the teachings of U.S. Patent Application Publication No. 2012/0232333 in combination with one or more or all of the teachings detailed herein.

There are some scenarios where such operating conditions are often not directly observable/are not directly observed even though they might be able to be directly observed utilizing certain components that might not be present in the hearing prostheses. That is, the operating conditions form a latent parameter. Accordingly, the system is operative to estimate this latent parameter for purposes of adapting to current operating conditions. Stated otherwise, the system utilizes a latent variable adaptive filter.

In an exemplary embodiment, the latent variable adaptive filter (LVAF) is computationally efficient, converges quickly, can be easily stabilized, and its performance is robust in the presence of correlated noise. It can be based on IIR filters, but rather than adapting all the coefficients independently, it can utilize the functional dependence of the coefficients on a latent variable. In statistics, a latent variable is one which is not directly observable, but that can be deduced from observations of the system. An example of a latent variable is the thickness of the tissue over the microphone and/or wave propagation properties through the tissue over the microphone. In at least some exemplary embodiments, this is not directly measured, but instead is deduced from the change in the microphone motion sensor (i.e., mic/acc) transfer function. Another hidden variable may be user "posture." It has been noted that some users of implantable hearing instruments experience difficulties with feedback when turning to the left or the right (usually one direction is worse) if the (nonadaptive) cancellation filter has been optimized with the recipient facing forward. Posture could be supposed to have one value at one "extreme" position, and another value at a different "extreme" position. "Extreme," in this case, is flexible in meaning; it could mean at the extreme ranges of the posture, or it could mean a much more modest change in posture that still produces different amounts of feedback for the recipient. Posture in this case can be a synthetic hidden variable (SHV), in that the actual value of the variable is arbitrary; what is important is that the value of the hidden variable changes with the different measurements. For instance, the value of the SHV for posture could be "+90" for the recipient facing all the way to the right, and "−90" for a recipient facing all the way to the left, regardless of whether the recipient actually rotated a full 90 degrees from front. The actual value of the SHV is arbitrary, and could be "−1" and "+1," or "0" and "+1" if such ranges lead to computational simplification.

It is noted that while the teachings detailed herein relating to the parameters are described in terms of the embodiments where the parameters are posture parameters, the parameters can be other parameters. Indeed, in an exemplary embodiment, the noise cancellation sub-systems detailed herein and/or variations thereof can track any impairment of the system, at least as long as the presence of the impairment can be detected. For example, an impairment could arise from for example an overflow of an internal register which, in some instances can cause oscillations in the outputs.

In the case of posture, in an exemplary embodiment, a physical parameter(s) are assigned to the SHV, such as the angle that the recipient is turned from facing forward. However, there are other cases in which the variable is truly hidden. An example might be where the recipient activates muscle groups internally, which may or may not have any external expression. In this case, if the tonus and non-tonus conditions affect the feedback differently, the two conditions could be given values of "0" and "+1," or some other arbitrary values. One of the advantages of using SHVs is that only the measurements of the vibration/motion response of the microphone assembly need to be made, it may be utilitarian not to measure the actual hidden variable. That is, the hidden variable(s) can be estimated and/or deduced.

As shown in FIG. 4, the adaptive system can utilize two adaptive cancellation filters 90 and 92 instead of one fixed cancellation filter. The cancellation filters are identical and each cancellation filter 90, 92, can include an adaptive filter (not shown) for use in adjusting the motion accelerometer signal, Acc, to match the microphone output signal, Mic, and thereby generate an adjusted or filtered motion signal. Additionally, each cancellation filter can include a summation device (not shown) for use in subtracting the filtered motion signals from the microphone output signals and thereby generate cancelled signals that are an estimate of the microphone response to desired signals (e.g., ambient acoustic signals). Each adaptive cancellation filter 90, 92 estimates a latent variable 'phi', a vector variable which represents the one or more dimensions of posture or other variable operating conditions that change in the recipient, but whose value is not directly observable. The estimate of the latent variable phi is used to set the coefficients of the cancellation filters to cancel out microphone noise caused by, for example, feedback and biological noise. That is, all coefficients of the filters 90, 92 are dependent upon the latent variable phi. After cancellation, one, both or a combination of the cancelled microphone signals, essentially the acoustic signal, are passed onto the remainder of the hearing instrument for signal processing.

In order to determine the value of the latent variable phi that provides the best cancellation, the coefficients of the first cancellation filter 90 are set to values based on an estimate of the latent variable phi. In contrast, the coefficients of the second cancellation filter 92, called the scout cancellation filter 92, are set to values based on the estimate of the latent variable phi plus (or minus) a predetermined value delta. Alternatively, the coefficients of the first filter 90 may be set to values of the latent variable plus delta and the coefficients of the second filter may be set to values of the latent variable minus delta. In this regard, the coefficients of the second adaptive filter 92 are slightly different than the coefficients of the first filter 90. Accordingly, the energies of the first and second cancelled signals or residuals output by the first and second adaptive cancellation filters 90, 92 may be slightly different. The residuals, which are the uncancelled portion of the microphone signal out of each cancellation filter 90, 92, are compared in a comparison module 94, and the difference in the residuals are used by the Phi estimator 96 to update the estimate of phi. Accordingly, the process may be repeated until the value of phi is iteratively determined. In this regard, phi may be updated until the residual value of the first and second cancellation filters is substantially equal. At such time, either of the cancelled signals may be utilized for subsequent processing, or, the cancelled signals may be averaged together in a summation device 98 and then processed.

Adjustment of the latent variable phi based on the comparison of the residuals of the cancelled signals allows for quickly adjusting the cancellation filters to the current operating conditions of the implantable hearing instrument. To further speed this process, it may be utilitarian to make large adjustments (i.e., steps) of the latent value, phi. For instance, if the range of the phi is known (e.g., 0 to 1) an initial mid-range estimate of phi (e.g., ½) may be utilized as a first estimate. Alternatively, the initial values of phi can be set at 0 (which can correspond to a relaxed posture, with respect to embodiments where phi is related to posture), and iteration proceeds from those values.

Likewise, the step size of the adjustment of phi may be relatively large (e.g., 0.05 or 0.1) to allow for quick convergence of the filter coefficients to adequately remove noise from the microphone output signal in response to changes in the operating conditions.

In order to implement the system of FIG. 4, in at least some embodiments, a filter is generated where the filter coefficients are dependent upon a latent variable that is associated with variable operating conditions/environment of the implantable hearing instrument. FIGS. 5-8 provide a broad overview of how dependency of the adaptive filter on varying operating conditions can be established in at least some embodiments.

Figure 5:
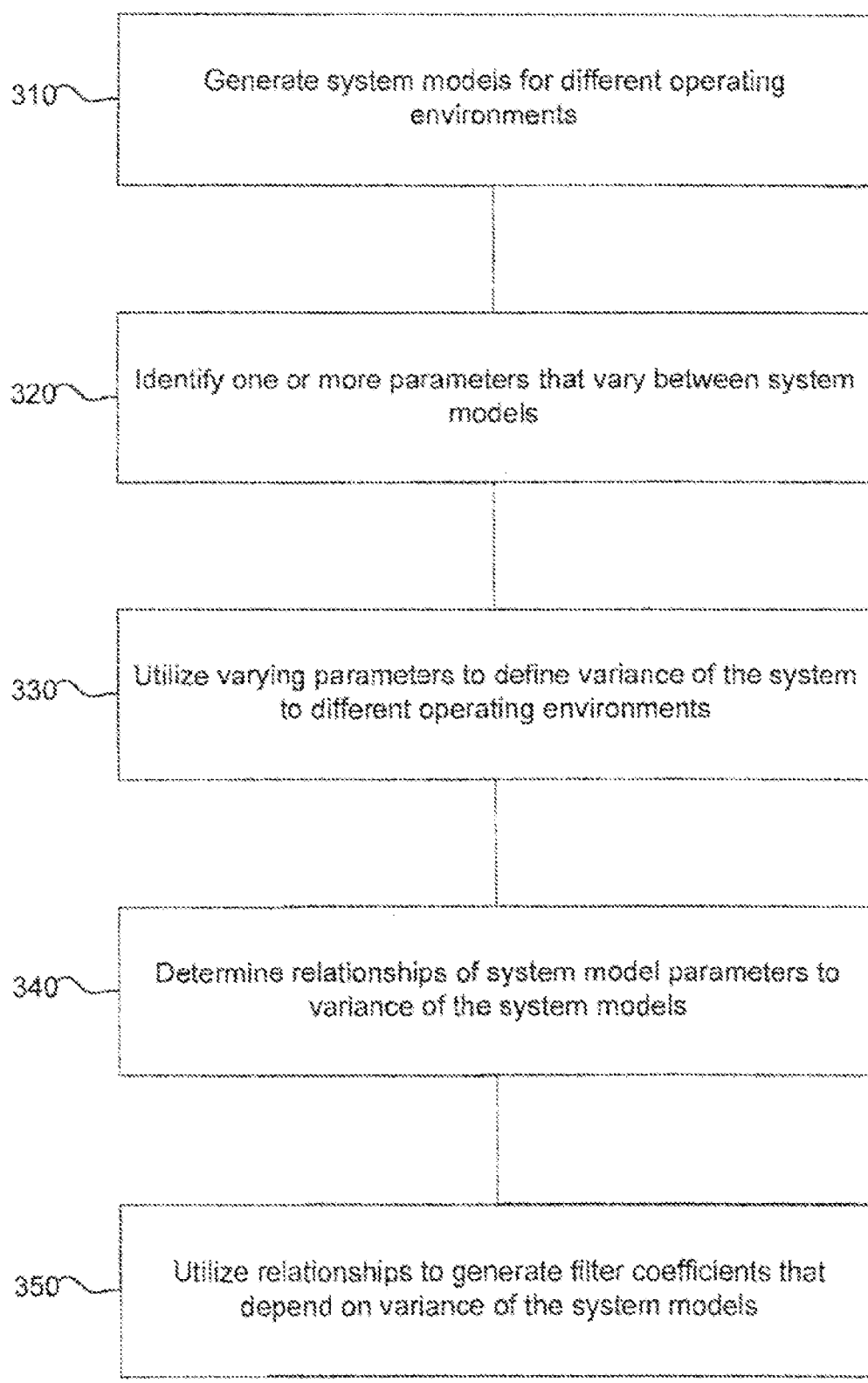
FIG. 5 depicts an exemplary flow chart according to an exemplary process.

FIG. 5 illustrates an overall process for generating the filter. Initially, the process requires two or more system models be generated for different operating environments. For instance, system models can be generated while a recipient is looking to the left, straight ahead, to the right and/or tilted. The system models may be generated as discussed above and/or as discussed in U.S. Patent Application Publication No. 20120232333 and/or according to any utilitarian methodology. Once such system models are generated at action 310, parameters of each of the system models may be identified at action 320. Specifically, parameters that vary between the different system models and hence different operating environments can be identified at action 320.

Figure 6:
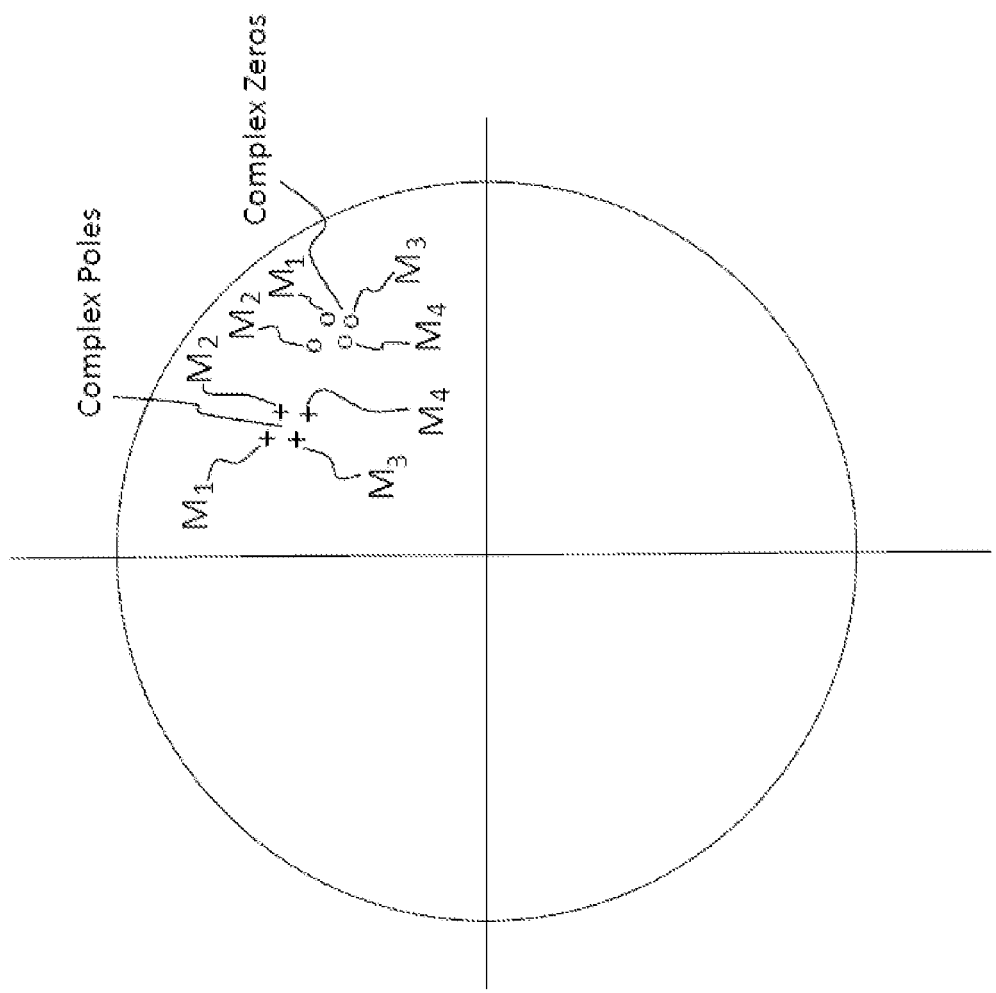
FIG. 6 depicts a plot of operating parameters in a unit circle.
Figure 7:
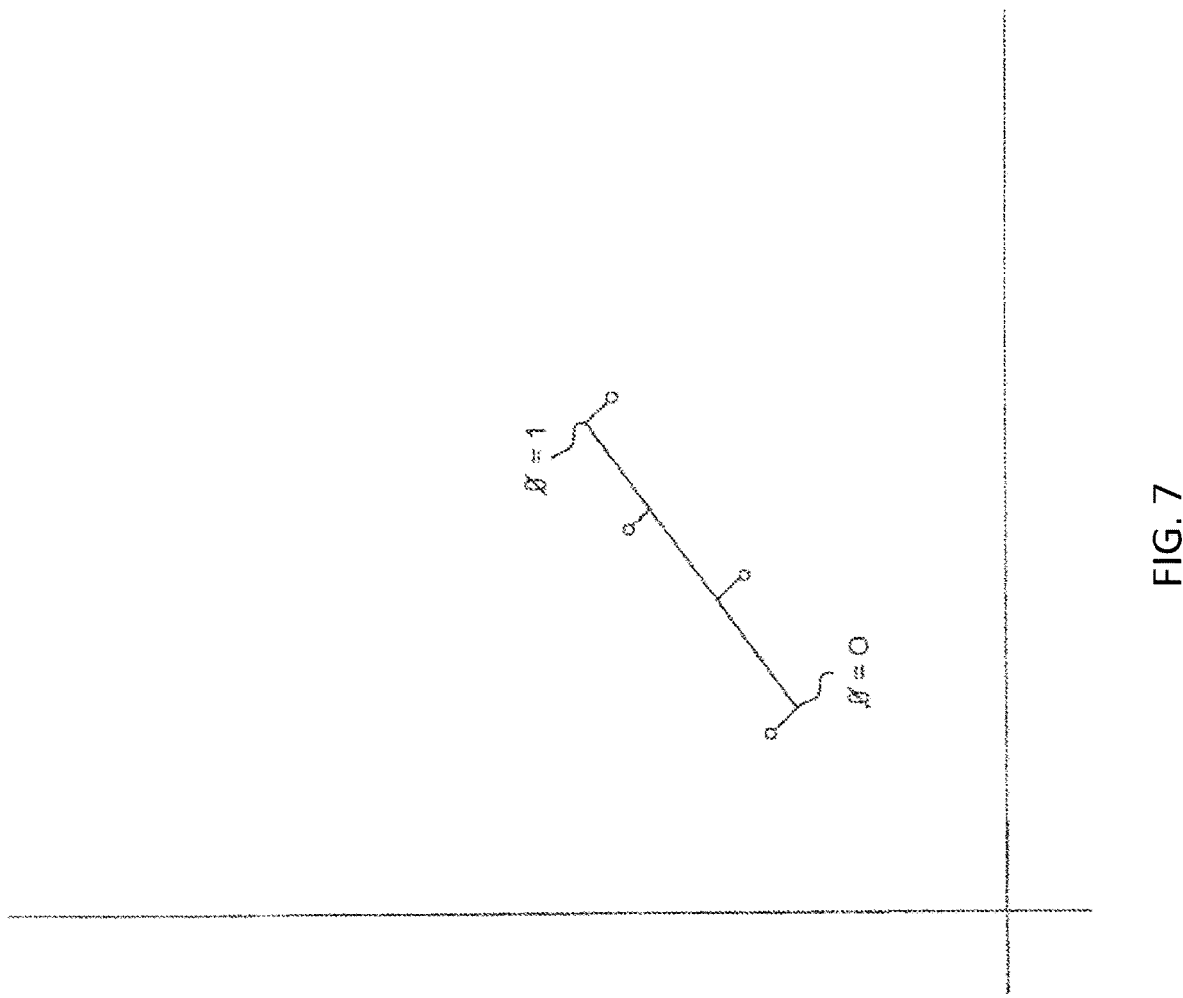
FIG. 7 illustrates the fitting of a line to a first set of operating parameters to define a range of a latent variable.

For instance, each system model can include multiple dimensions. Such dimensions may include, without limitation, gain, a real pole, a real zero, as well as complex poles and zeros. Further, it will be appreciated that complex poles and zeros may include a radius as well as an angular dimension. In any case, a set of these parameters that vary between different models (i.e., and different operating environments) may be identified. For instance, it may be determined that the complex radius and complex angle and gain (i.e., three parameters) of each system model show variation for different operating conditions. For instance, FIG. 6 illustrates a plot of a unit circle in a "z" dimension. As shown, the complex zeros and complex poles for four system models $M_1$ to $M_4$ are projected onto the plot. As can be seen, there is some variance between the parameters of the different system models. However, it will be appreciated that other parameters can be selected. In at least some embodiments, the parameters that are selected are selected such that they vary between the system models and this variance is caused by change in the operating condition of the implantable hearing instrument.

Figure 8:
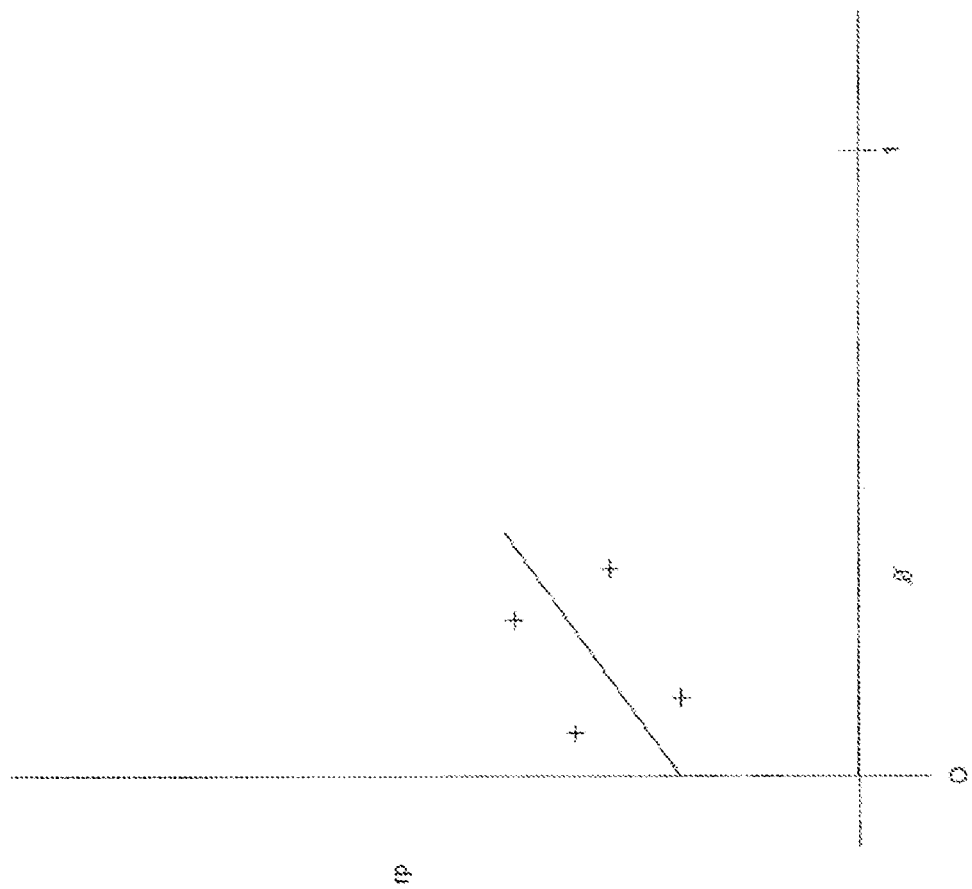
FIG. 8 illustrates a linear regression analysis of system parameters to the latent variable.

Once the variable parameters are identified at action 320, they can be projected onto a subspace (action 330). In the present arrangement, where multiple parameters are selected, this can entail executing a principle component analysis on the selected parameters in order to reduce their dimensionality. Specifically, in the present embodiment, principle component analysis is performed to reduce dimensionality to a single dimension such that a line can be fit to the resulting data points. (See, for example, FIG. 7.) Accordingly, this data can represent operating environment variance or latent variable for the system. For instance, in the present arrangement where four system models are based on four different postures of the user, the variance can represent a posture value. Further, the plot can define the range of the latent variable. That is, a line fit to the data may define the limits of the latent invariable. For instance, a first end of the line may be defined as zero, and the second end of the line may be defined as one. At this point, a latent variable value for each system model may be identified. Further, the relationship of the remaining parameters of each of the system models can be determined relative to the latent variables of the system models (e.g., action 340). For instance, as shown in FIG. 8, a linear regression analysis of all the real poles of the four system models to the latent variable may be projected. In this regard, the relationship of each of the parameters (i.e., real poles, real zeros, etc.) relative to the latent variables may be determined. For instance, a slope of the resulting linear regression may be utilized as a sensitivity for each parameter. Accordingly, this relationship between the parameters and the latent variable are determined, this information may be utilized to generate a coefficient vector, where the coefficient vector may be implemented with the cancellation filters 90, 92 of the system of FIG. 4 (action 350). As will be appreciated, the coefficient vector will be dependent upon the latent variable. Accordingly, by adjusting a single value (the latent variable), all of the coefficients may be adjusted.

Further details of noise cancellation implementation that can be used in some embodiments is found in US Patent Application Publication No. 2015/0256949 published on Sep. 10, 2015, naming Filiep J. Vanpoucke as an inventor. In this regard, at least some embodiments include devices, systems and/or methods that utilize one or more or all of the teachings of U.S. Patent Application Publication No. 2015/0256949 in combination with one or more or all of the teachings detailed herein.

Figure 9:
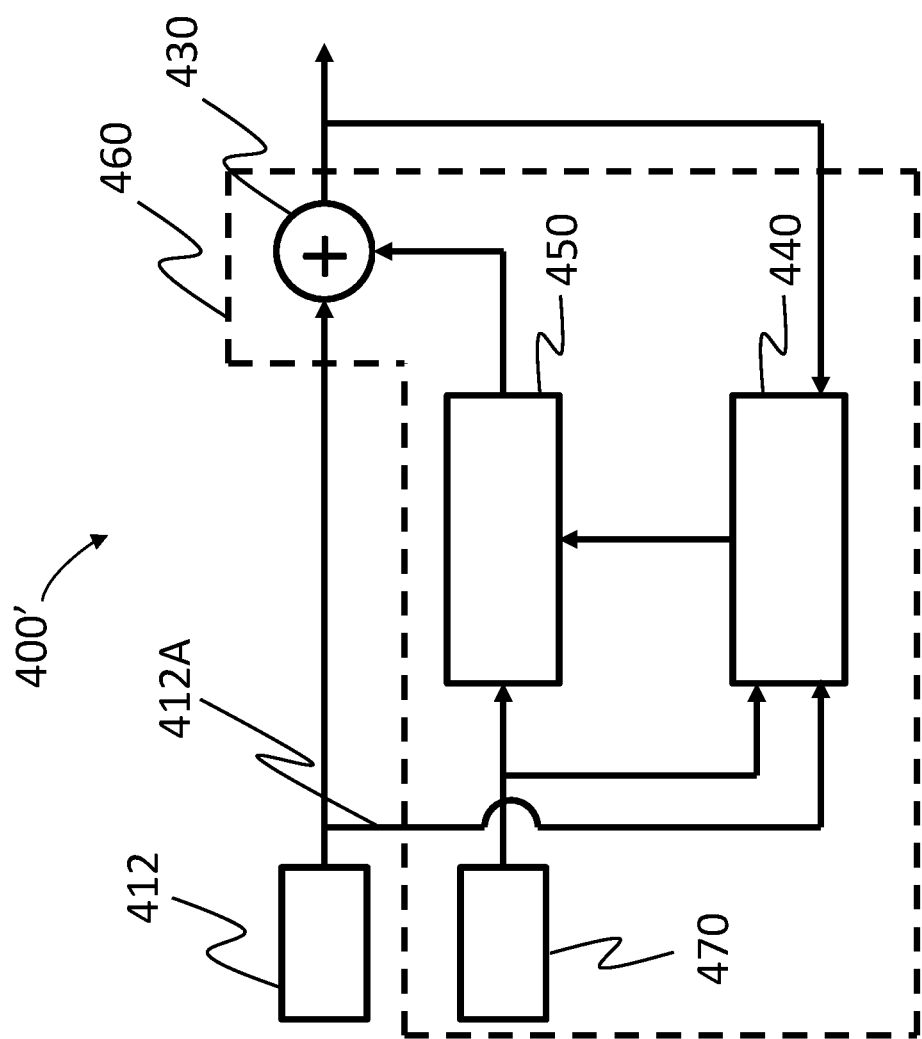
FIG. 9 functionally depicts another exemplary embodiment of a system that is usable in the hearing prosthesis of FIG. 1.

Accordingly, FIG. 9 depicts a system 400', which is a variation of the system 400 of FIG. 3B. It is noted at this time that any reference to system 400' corresponds to a reference to system 400, system 400" (discussed below) and system 400''' (also discussed below), unless otherwise noted, just as a reference to system 400" corresponds to a reference to system 400, 400', 400''', and so on. As can be seen, there is a direct signal route 412A from the microphone 412 to the filter control unit 440. Thus, the system 400' in general, and control unit 440 in particular, is configured to compare or otherwise evaluate the raw outputs of the microphone 412 and the accelerometer 470 and identify the presence of an own voice body event based on these raw outputs. That said, in an alternate embodiment, the outputs can be amplified and/or otherwise signal processed between the transducers and the control unit, or after the control unit, etc. In an embodiment of the system 400', the control unit 440 is configured such that it receives outputs from the transducers simultaneously without cancellation, even in the presence of noise cancellation. (Conversely, in the embodiments of FIG. 3B, the control unit 440 could simultaneously receive outputs from both the transducers without cancellation, but only in the absence of the noise cancellation. Still, in at least some embodiments of FIG. 3B, because the amount of cancellation resulting from the signal having passed through adder 430 is known, the output of microphone 412 without cancellation can be calculated by simply "adding" the equivalent of the canceled signal back into the signal that is received by the filter control unit 440 that originates downstream of the adder 430.)

In an exemplary embodiment of the system 400, the system is configured to compare a parameter that is related to transduced energy originating from the acoustic signal to a parameter related to transduced energy originating from the body noise. The system is further configured to identify the presence (and thus identify the absence) of an own of voice event based on the comparison. Some additional details of such an exemplary embodiment are described below.

Now with reference back to FIG. 3B, and in view of FIG. 3A, the system 400 is configured to cancel body noise energy from signal(s) output by the transducer system 480 that includes energy originating from the aforementioned acoustic signal (the ambient noise signal 103). In an exemplary embodiment, this cancellation of body noise is executed by the system 400 during some modes of operation, such as a mode of operation in which the system operates in the absence of an identification by the aforementioned control unit of an identification of the presence of the own voice body noise event. That is, in an exemplary embodiment, the system 400 is configured to alternately cancel body noise energy from the transducer signal depending on a mode of operation. In this regard, if the system 400, via the control unit 440, does not identify the presence of an own voice event and/or identifies the absence of an own voice event, the system operates to cancel body noise. (In an exemplary embodiment, it operates to cancel body noise according to the adaptive methods, systems, and/or devices detailed herein and/or variations thereof.) That said, this does not exclude the cancellation of body noise energy from the transducer signal during the mode of operation where the control unit identifies the presence of an own voice body noise event, although in some embodiments, the system is so configured such that cancellation of body noise energy from the transducer signal is suspended during such a mode of operation.

It is noted that some embodiments of the just-detailed embodiment are compatible with at least some of the aforementioned teachings above. Thus, in an exemplary embodiment, at least some of the aforementioned teachings are combined with such an embodiment. In this vein, in an exemplary embodiment, the system 400 (or 400', etc.) is configured to cancel body noise energy from the transducer signal that includes energy originating from the acoustic signal differently/in a different manner, depending on whether the control unit has identified the presence (or absence) of the own voice body noise event. That is, the cancellation of body noise energy from the transducer signal upon an identification of the presence of the own voice event is performed differently from that which would be the case in the absence of the identification of the presence of the own voice event.

Still with reference to FIG. 3B, there is an exemplary embodiment of the system 400 that adjusts a mixing ratio of outputs from the microphone 412 and the accelerometer 470 on the identification of an own voice body noise event. More particularly, microphone 412 is configured to transduce energy originating at least in part from the acoustic signal, and accelerometer 470 is configured to transduce energy originating from body noise, where the latter is effectively isolated from energy originating from the acoustic signal concomitant with the teachings detailed above associated with the accelerometer. In this embodiment, the noise cancellation system 460 (whether it be in adaptive noise cancellation system or a standard (nonadaptive) noise cancellation system), is configured to affect the cancellation of the body noise energy from a transducer signal (e.g., the output from the microphone 412) that includes the energy originating from the acoustic signal. The system is further configured to adjust a cancellation system mixing ratio of output from the microphone 412 and output from the accelerometer 470 upon the identification of the own voice event. In the embodiment of FIG. 3B, the cancellation system mixing ratio is adjusted by adjusting the adjustable filters 450, which, in at least some embodiments, adjusts the magnitude of the signal passed therethrough. That said, in an alternate embodiment, a separate component can be utilized to adjust the mixing ratio. In an exemplary embodiment, adder 430 is controlled to adjust the mixing ratio.

Some exemplary embodiments have utilitarian value by being configured to adjust the mixing ratio such that output from the accelerometer 470 has less influence on the cancelation system relative to that which would be the case in the absence of the identification of the own voice event. In an exemplary embodiment, the mixing ratio can be reduced to zero such that the output from the accelerometer 470 has no influence on the cancellation system relative to that which would be the case in the absence of the identification of the own voice event.

In view of the above, some exemplary embodiments can be considered in terms of a hearing prosthesis having a noise cancellation system in general, and an adaptive noise cancellation system in particular, with a flexible sound path. Some specific embodiments of such exemplary embodiments will now be described in terms of varying this "sound path." However, it is noted that in alternative embodiments, signal processing techniques can be utilized to achieve the same and/or similar effects. In this regard, any disclosure herein relating to the variation and/or adjustment of a sound path to enable the teachings detailed herein and/or variations thereof also corresponds to a disclosure of utilizing a sound processor system to achieve that functionality and/or variation thereof.

With reference to FIGS. 3B and 9, as can be seen, the sound path between the microphone 412 and the downstream side of the adder 430 (which can lead to a signal processor and/or an output device, as detailed above) can be influenced by the adder 430. In some embodiments, the functionality of this adder can be disabled, such that the signal from microphone 412 passes to components downstream of the system depicted in FIGS. 3B and 9 (e.g., a stimulator of an electrode array, an actuator, a sound processor, etc.) without cancellation by the noise cancellation subsystem 460. In a variation of this concept, a signal path can be provided that completely bypasses the adder 430 via the use of switching or the like. That is, for example, the signal from the microphone 412 can be sent through adder 430, or can be switched to bypass the adder 430. Still further, in a variation of this concept, the output of the microphone 412 can include a path to the adder 430 and a path that bypasses the adder 430, and the switching unit can be utilized to switch between these two paths to control which signal (a signal subjected to noise cancellation or a raw/noncancelled signal) is delivered to the components downstream of the system 400/400'.

In at least some exemplary embodiments, if the control unit 440 (which can correspond to a classifier that classifies the outputs of the transducers as having own voice body noise content or not having own voice body noise content), or other control unit separate from the control unit 440, determines that there exists an own voice body noise content to the outputs of the microphone 412 and/or the accelerometer 470, the control unit 440 can control the system such that no noise cancellation takes place. (In an exemplary embodiment, this can entail eliminating the outputs of filters 450 to adder 430 and/or bypassing the adder 430 according to the aforementioned switching techniques etc.) Otherwise, in the absence of a determination of the presence of own voice body noise, the control unit 440 controls the system such that noise cancellation takes place in a normal manner to cancel out generally as much of the body noise as technology can enable. That said, in an alternate embodiment, if a determination is made that there exists the presence of own voice body noise, the control unit 440 can control the system such that less noise cancellation takes and/or the noise cancellation that takes place is different from that which would be the case in the absence of such a determination.

In this regard, an exemplary embodiment can have utility in that the lack of cancellation of own voice body noise from the signal from the microphone 412 (or cancellation in a different manner from the normal scenario)/the inclusion of own voice body noise (or a portion of such) in the signal that is outputted from the system 400/400', and the subsequent utilization of those signals to evoke a hearing percept, can result in a more natural hearing percept. In this regard, normal hearing persons hear their own voice via tissue conduction (bone/skin conduction etc.). This is why one can hear themselves speak even though he or she covers his or her ears. Canceling own voice body noise with the goal of reducing the effect of unwanted body noise to achieve a more normal hearing percept can, in some instances, actually cause a hearing percept that sounds less normal than otherwise might be the case. Put another way, some embodiments of this embodiment can have utility in that it can enable a hearing impaired person to have a hearing percept that has a content corresponding to his or her own voice resulting from tissue conduction. This can be in addition to the hearing percept that has a content corresponding to his or her own voice resulting from air conduction (i.e., content resulting from pressure waves exiting the mouth of the recipient resulting from speaking, etc., and traveling through the air to impinge upon the skin of the recipient, and then conducted through the skin of the recipient to the microphone 412, where it is transduced into an output signal). Conversely, completely and/or substantially eliminating all body noise from the output of the systems, including eliminating own voice body noise, can result in a unnatural sound, which can be annoying or otherwise irritating, at least to recipients who have previously had natural hearing. This can result in a hearing percept having an echo character and/or can result in a hearing percept aware the recipient has a percept of his or her own voice, but that percept has a "boomy" quality to it. Thus, an exemplary embodiment can provide a hearing percept where these features are mitigated and/or eliminated.

Continuing with reference to FIGS. 3B and 9, in an exemplary embodiment, the signal path between microphone 412 and the adder 430 and/or the signal path between microphone 412 and the output of the systems 400/400' is configured such that the output of that path results in a hearing percept that has balance between the recipient's own voice and external sounds, including external speech. In an exemplary embodiment, the signal path is optimized for such balance. That is, in an exemplary embodiment, the signal path is established such that the hearing percept resulting from a non-noise canceled signal corresponds more closely to a normal hearing experience, at least in the absence of non-own voice body noise, relative to that which would be the case if noise cancellation took place (at least aggressive/full noise cancellation implementation). In some embodiments, the aforementioned path results in broad band attenuation, where the amount of attenuation is tuned for balance between own voice content and external sounds, including external speech. In an exemplary embodiment, this can have utility in that a broadband attenuator can have a spectral balance of own voice content that is not altered or otherwise limited in its alteration, and thus retaining natural quality, or at least a quality relatively closer to that more natural quality.

Further details of variations of the embodiment of FIG. 9 are found in US Patent Application Publication No. 2015/0256949 published on Sep. 10, 2015, naming Filiep J. Vanpoucke as an inventor.

Figure 10:
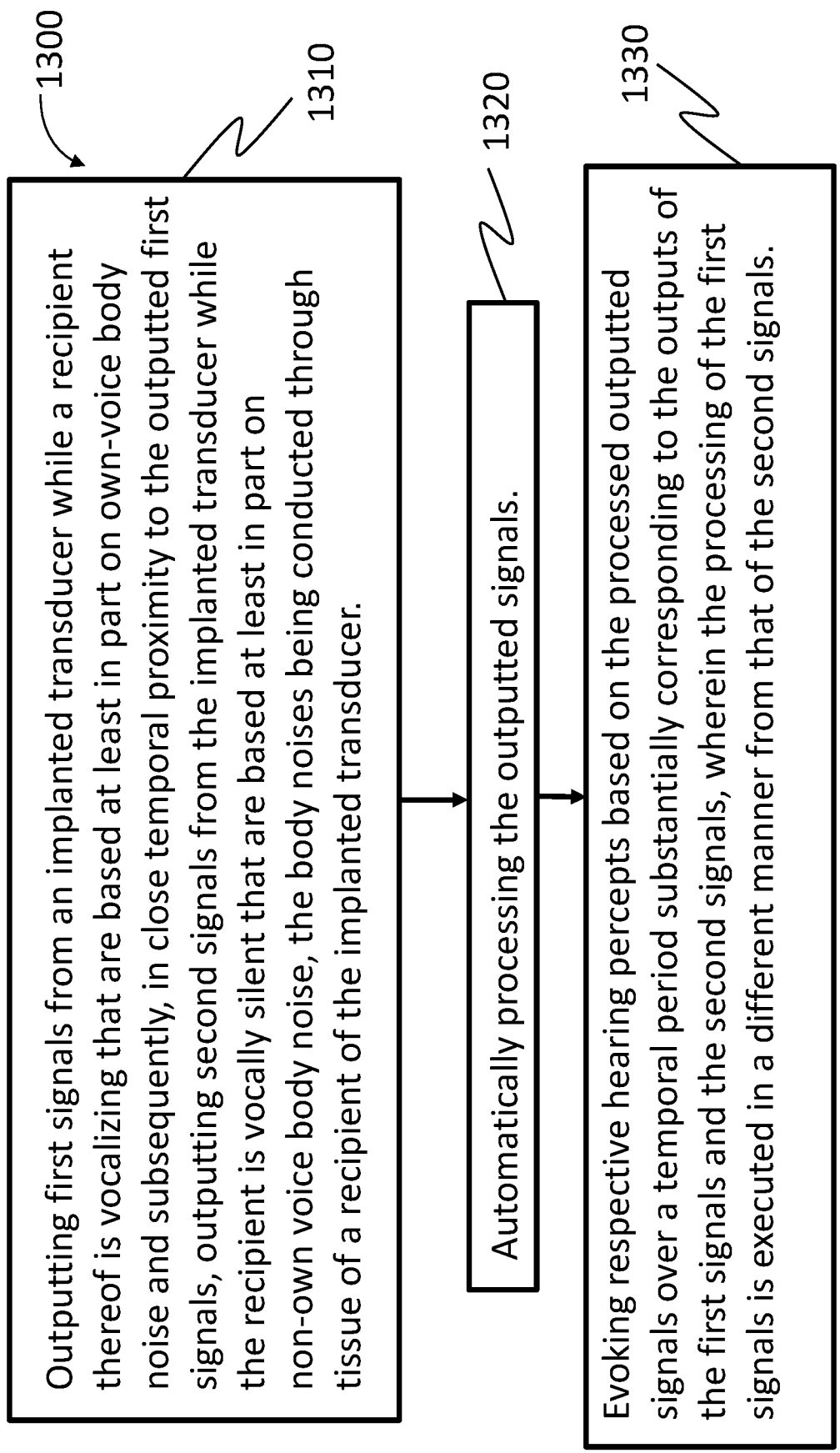
FIG. 10 depicts an exemplary flowchart according to an exemplary embodiment.

Referring now to FIG. 10, which presents an exemplary algorithm 1300 according to an exemplary method, there is a method that entails an action 1310 of outputting first signals from an implanted transducer (e.g., microphone 412) while a recipient is vocally silent (i.e., not making sounds associated with utilization of the vocal cords, and thus not generating own voice body noise). These first signals are based at least in part on non-own voice body noise, although in an exemplary embodiment, the first signals are totally based on non-own voice body noise. Action 1310 entails subsequently, in close temporal proximity to the outputted first signals (e.g., within the temporal boundaries of a conversation, within tens of seconds, etc.), outputting second signals from the implanted transducer while the recipient is vocalizing (i.e., making sounds associated with utilization of the vocal cords) that are based at least in part on own voice body noise. It is noted that in alternate embodiments, action 1310 is not so temporally restricted. Instead, the temporal proximity relates to a minute or two. In some embodiments, there is no temporal restriction. In action 1310, the body noises are conducted through tissue of a recipient of the implanted transducer. In action 1310, in at least some embodiments, when the recipient is vocally silent, and thus not generating own voice body noise, the outputted first signals outputted from the implanted transducer are not based on own voice body noise.

It is noted that in at least some embodiments, the first signals and/or second signals can be based, at least in part, on the acoustic signal/ambient noise that results in pressure waves in impinging upon the surface of the skin of the recipient, wherein these pressure waves cause subsequent pressure waves to travel through skin of the recipient to the implantable transducer, such that the implantable transducer transduces the ambient sound.

Algorithm 1300 includes an action 1320 of automatically processing the outputted signals from the implanted transducer, with the caveat below. Action 1320 can be accomplished utilizing a sound processor and/or any type of system that can enable automated processing of the outputted signals to execute the method of algorithm 1300. It is noted that by "processing the outputted signals," it is meant both the processing of signals that are outputted directly from the microphone 412, and the processing of signals that are based on the output from the microphone 412.

Algorithm 1300 further includes action 1330, which entails evoking respective hearing percepts based on the processed outputted signals over a temporal period substantially corresponding to the outputs of the first signals and the second signals, wherein the processing of the first signals is executed in a different manner from that of the second signals. By way of example only and not by way of limitation, processing of signals in a different manner from that of the second signals can entail any of the regimes detailed herein and/or variations thereof associated with managing otherwise addressing the own voice body noise phenomenon.

Additional features that can be executed with method 1300 are detailed in US Patent Application Publication No. 2015/0256949 published on Sep. 10, 2015, naming Filiep J. Vanpoucke as an inventor.

Figure 11:
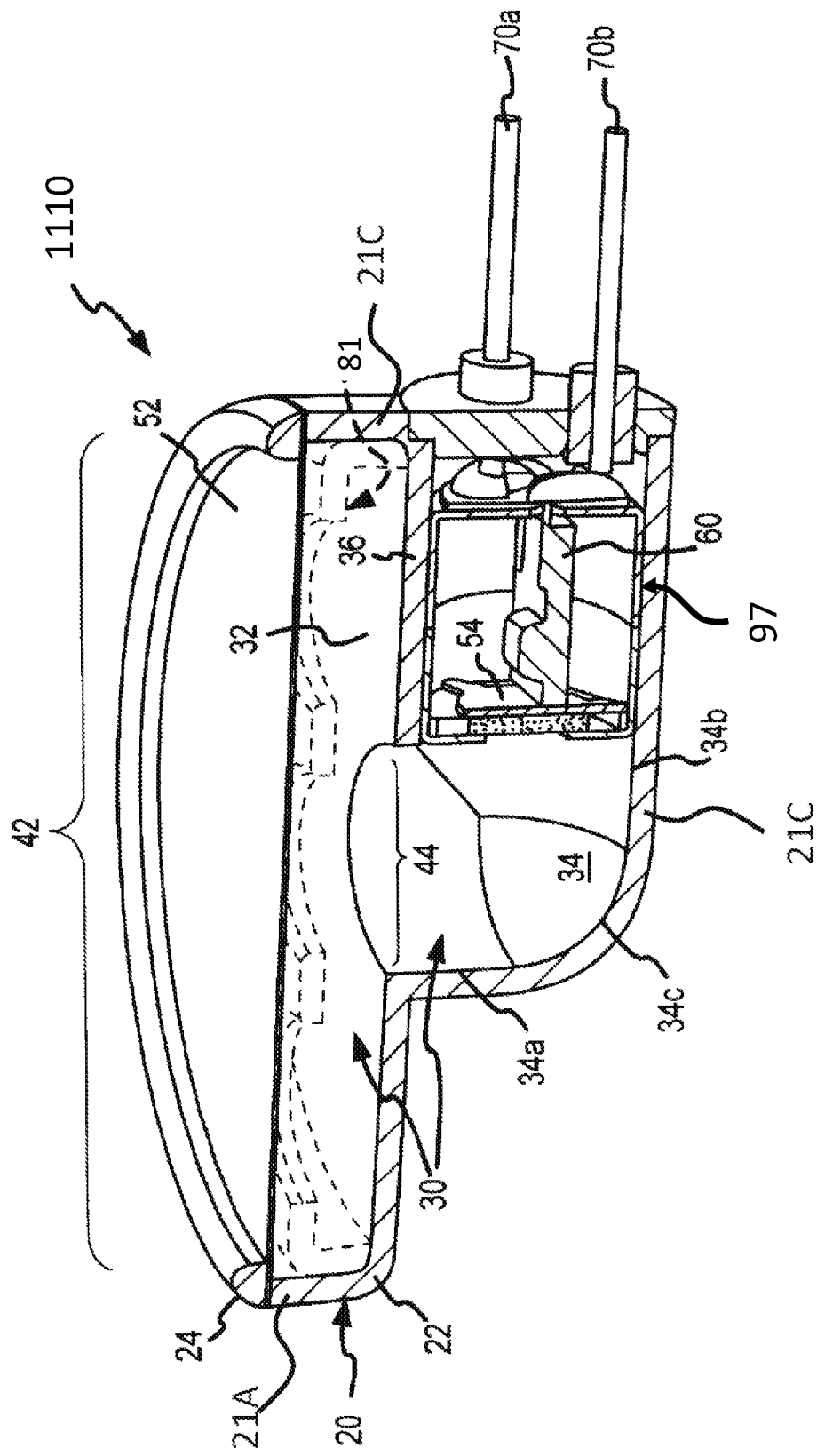
FIGS. 11-13 depict some exemplary teachings associated with a microphone that are usable in some embodiments.

FIG. 11 depicts a cross-sectional view of an exemplary implantable microphone 1110, which can correspond to microphone 12/412 above. The microphone 1110 includes a housing 20 that defines an internal chamber 30. The chamber 30 has an aperture 42 across which a first diaphragm 52 is sealably disposed. Housing 20 includes a base member 22 and a peripheral member 24 defining the aperture 42. The peripheral edge of the first diaphragm 52 is fixedly interconnected between the base member 22 and peripheral member 24 of the housing 20 (e.g., via laser welding). The peripheral member 24 and the diaphragm 52 are the two components of the microphone 1110.

The diaphragm 52 can be welded to the housing 20. This weld can establish a hermetic seal between the exposed portions of the microphone 1110 such that the interior of the microphone is hermetically sealed from the ambient environment.

Figure 12:
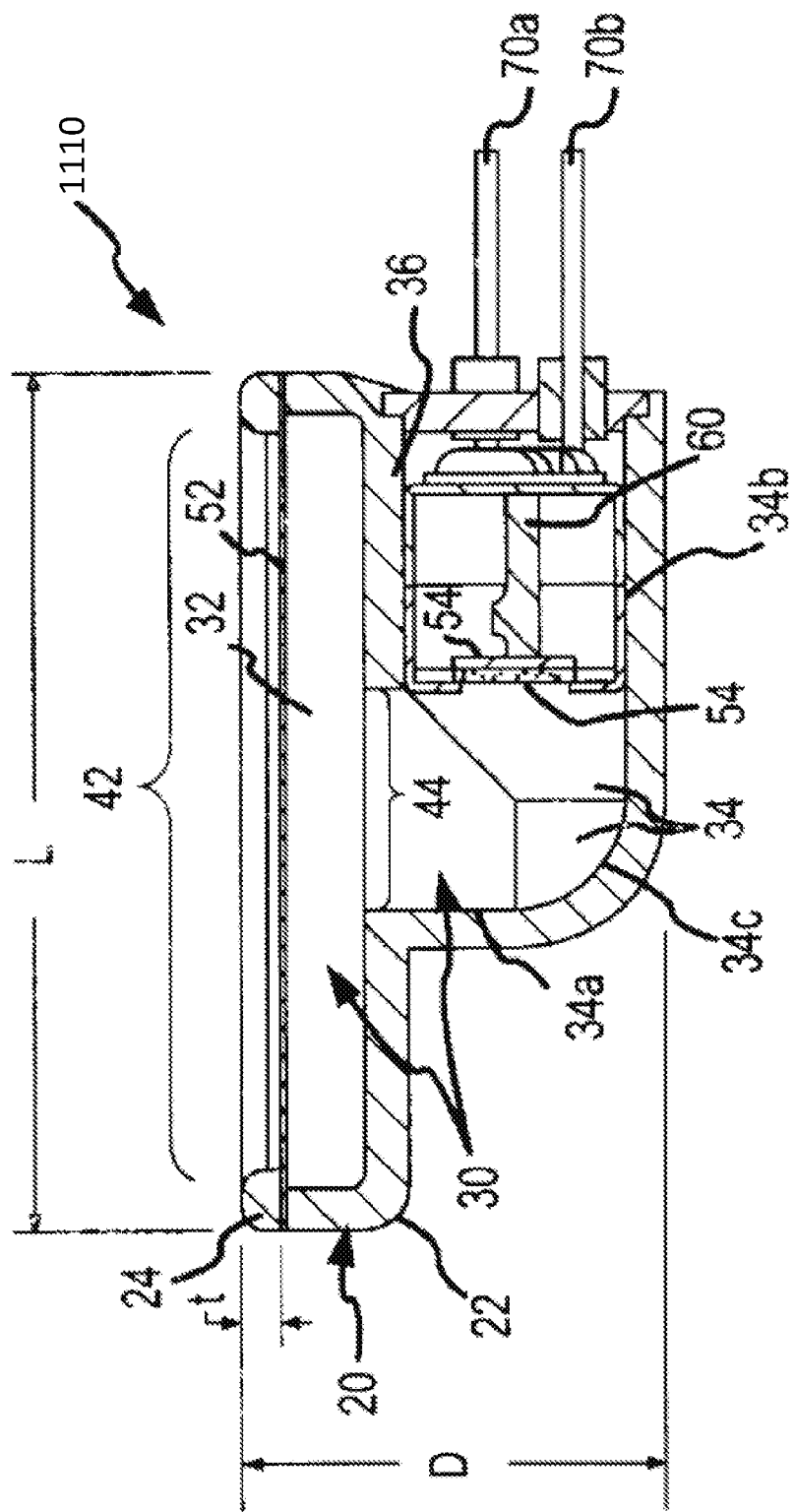

Referring now to FIG. 12, the first diaphragm 52 is recessed relative to the outer peripheral member 24. In this regard, in at least some exemplary embodiments there is utilitarian value if the first diaphragm 52 is recessed a distance t relative to the outer rim of peripheral member 24. In an exemplary embodiment, t is greater than 0.5 mm and/or less than 1.0 mm.

As illustrated in FIGS. 11 and 12, internal chamber 30 can be provided to include a first portion 32 and a second portion 34. The first portion 32 is disposed adjacent to the first diaphragm 52. The second portion 34 adjoins and extends away from the first portion 32 at an opening 44 therebetween and about an axis that is transverse to the first diaphragm 52 and aperture 42. As shown, opening 44 can be of a reduced cross-sectional area relative to aperture 42.

In the microphone 1110, the second internal chamber portion 34 can be of L-shaped configuration, wherein the second portion 34 comprises a first leg 34a that extends away from the first internal chamber portion 32 about an axis that is substantially perpendicular to a center plane of the first diaphragm 52. The second internal chamber portion 34 further includes a second leg 34b interconnected to the first leg 34a at a rounded elbow 34c.

Aperture 42 and opening 44 can each be of a circular configuration and can each be aligned about a common center axis. Correspondingly, such common center axis can be aligned with a center axis for first diaphragm 52 which can also be of a circular shape. Further, the first internal chamber portion 32 and first leg 34a of the second internal chamber portion 34 can each be of a cylindrical configuration, and can each be aligned on the same center axis as aperture 42 and opening 44. The second leg 34b of the second portion 34 of chamber 32 can be disposed to extend substantially perpendicularly from the first leg 34a of the second portion 34. As such, it can be seen that the second leg 34b may share a wall portion 36 with the first portion 32 of the internal chamber 30.

As shown in FIGS. 11 and 12, there is a second diaphragm 54 that is disposed at the interface between the first leg 34a and second leg 34b of the second chamber portion 34. More particularly, the second diaphragm 54 can be provided at a port of a conventional hearing aid (corresponding to microphone element 60) which is disposed within the second leg 34b of the second chamber portion 34. In this regard, microphone element 60 can comprise an electret transducer in the form of an electret condenser microphone. In this regard, the second diaphragm 54 can be provided as part of the conventional hearing aid microphone. Microphone element 60 can be provided with electrical power and control signals and may provide an electrical output signal, each of which signals are carried by corresponding signal lines 70a, 70b or 70c. Collectively, components 54 and 60 and the support structure therefore form a transducer microphone element assembly 97.

In use, the microphone 10 can be surgically implanted in the mastoid region of a patient, wherein the aperture 42 and the first diaphragm 52 are positioned immediately adjacent to and facing the skin of the patient. Upon receipt of vibrations traveling through the skin of the recipient resulting from an acoustical signal impinging upon the outside of the recipient's skin as a result of an ambient noise, first diaphragm 52 will vibrate to act upon the enclosed volume within chamber 30 and thereby pass the vibration from one side of the first diaphragm 52 (the outside) into the chamber 30 such that it is communicated by the medium therein and received by the second diaphragm 54.

Upon receipt of vibrational energy traveling through internal chamber 30 originating from movement of the diaphragm 52 and impinging upon the second diaphragm 54, the microphone element 60 converts the energy impinging thereupon into an electrical signal for output via one of the signal lines 70a, 70b or 70c. In turn, such output signal can be further conditioned and/or directly transmitted to a sound processor or the like of the hearing prosthesis of which the microphone 10 is apart.

The housing 20 and first diaphragm 52 can be constructed from biocompatible materials. In particular, titanium and/or biocompatible titanium-containing alloys may be utilized for the construction of such components. With particular respect to the first diaphragm 52 in an exemplary embodiment, the material utilized and thickness thereof can be such that it yields resonant frequency above about 3.5 kHz when mechanically loaded by tissue, wherein the resonance has, in at least some embodiments no greater than about a 20 dB excursion. Further, attenuation effects of the first diaphragm 52 can be, in at least some embodiments, more than 10 dB from about 250 Hz to 5.5 kHz. By way of example, first diaphragm 52 can comprise titanium, and may be of a flat, disk-shaped configuration having a thickness of between about 5 to about 20 microns. In an exemplary embodiment, there is a diaphragm having a 10 or 15 micron thickness that is under tension of about 400 N/m. However, in an alternate embodiment, the first diaphragm 52 is instead a plate, such as a titanium plate, having a thickness of more than 20 microns. In an exemplary embodiment, the diaphragm (or plate) has a material utilized and thickness thereof is such that it yields resonant frequency above about 9, 10, 11, 12, 13, 14, 15 or more kHz when mechanically loaded by tissue. In an exemplary embodiment, when element 52 is a plate, the plate can have a thickness of less than or equal to about 200 microns (in some embodiments, there is no tension on the plates). In an exemplary embodiment, there is a plate having a thickness of about 100 microns or less, or a plate having a thickness of about 32 microns or less. In an exemplary embodiment, the spring rate of the diaphragm is relatively small compared to the spring rate of the fluid inside the chamber. This results in the pressure loading being coupled to the microphone diaphragm in a relatively complete manner, rather than some of the force from the external pressure being supported by the diaphragm 52 and the housing 20 whereby the pressure loading can be lost.

Figure 13:
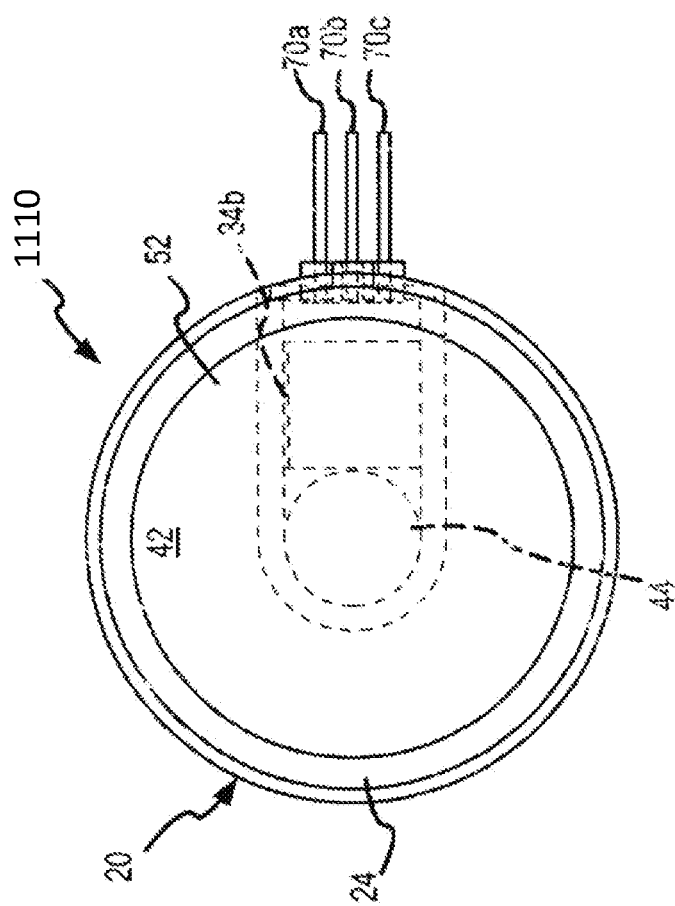

In an exemplary embodiment, there is a support member 81 that is located within the first portion 32 of the internal chamber 30 of housing 20, as is depicted by the phantom lines in FIG. 11. FIG. 13 depicts a top view of the microphone 1110.

Figure 14:
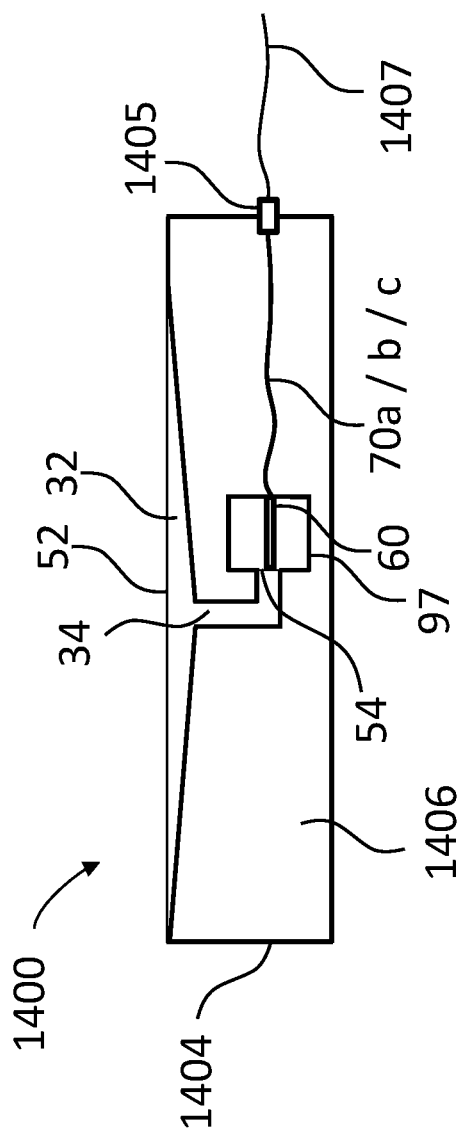
FIG. 14 depicts an exemplary embodiment in which some teachings herein can be utilized.

Microphone 1110 can be an integral part of an implanted unit, such as the implantable component 100. In an exemplary embodiment, the unit includes the microphone and a receiver-stimulator of a cochlear implant, a signal processor (sound processor) and/or other components. It is further noted that in alternative embodiments, the microphone 1110 can be located within the recipient at a location remote from the unit that includes the receiver-stimulator. That is, in an exemplary embodiment, microphone 1110 can be a separate, self-contained unit in signal communication with the unit that includes the receiver-stimulator, where the latter can also contain a signal processor (sound processor) and/or other components, the microphone 1110 being in signal communication with the remote unit via electrical leads, etc. An exemplary embodiment of a separate, self-contained microphone is seen in FIG. 14, depicting microphone 1400 (additional details will be discussed below). In such an exemplary embodiment, additional housing components might be utilized with microphone 1110 to achieve the functionality afforded by a self-contained unit hermetically enclosing portions of the microphone 1110 that might not be hermetically enclosed according to the configuration of FIG. 11 (although in other embodiments, the configuration of FIG. 11 presents a hermetic enclosure with respect to the at least the components establishing the outline of the microphone 1110 presented therein—where communication cables 70a and 70b can lead to feedthroughs hermetically connected to the housing 20 and/or can be hermetically sealed at junctions passing into the housing, the microphone element 60, etc.). Any implanted placement of the microphone 1110 that can enable the microphone 1110 to be utilitarianly utilized according to the teachings detailed herein and/or variations thereof can be utilized in at least some embodiments.

FIG. 14 depicts in a quasi-functional manner a self-contained microphone 1400 according to an exemplary embodiment. The microphone of FIG. 14 includes the features of the microphone 1110 detailed above in at least some exemplary embodiments. Indeed, in an exemplary embodiment, any disclosure herein of a microphone can include one or more or all of the features of microphone 1100. Like reference numbers have been utilized. This microphone can correspond to the microphone 12 above. As can be seen, the upper chamber 32 in this embodiment is conical shaped/funnel shaped, and the lower chamber 34 which leads from the throat of the funnel dog legs to the transducer microphone element assembly 97. Signal lines 70 a, b, and c lead to a feedthrough 1405 which in turn is connected to an electrical lead 1407 which is configured to be connected to a remote unit which can include a sound processor or the like. A connector (not shown) can be located at the end of lead 1407 to enable the microphone 1400 to be removably connected to the remote unit that includes the signal processor and also place the microphone 1402 why communication there with. A housing 1404 encloses the interior of the microphone 1400 and supports the diaphragm 52 directly or indirectly as the case may be. The feedthrough 1405 is part of a system that establishes a hermetically sealed interior 1406, which is hermetically isolated from the environment in which the microphone 1400 can be located (e.g., implanted inside a human beneath the skin thereof).

In view of the above, it can be seen that in an exemplary embodiment, there is an implanted/implantable microphone that employs a flexible diaphragm responsive to acoustic signals (outside sounds) that has a hermetic seal which prevents ingress of gas or liquid into the microphone enclosure. The diaphragm transmits pressure waves (compression and/or rarefaction) into the microphone enclosure, causing changes (which can be rapid) in pressure within a defined volume (the "front volume"—the volume established at least by chambers 32 and 34). These changes in pressure are detected in turn by a microphone element 60 located on an opposite side of a diaphragm 54 relative to the front volume) and so disposed as to face the front volume with its acoustically sensitive side. On the opposite side of the diaphragm 54 relative to the front volume is another defined volume (the "back volume"), which serves as an acoustic compliance area allowing the diaphragm 54 to deflect and detect sound from the front volume. The microphone element 60 is coupled to this diaphragm (directly or indirectly), and, in some embodiments, is connected to signal-processing circuitry (e.g. on a printed circuit board assembly, or "PCBA") and sealed to a partition in which it is mounted so as to prevent transmission of gas or working fluid from one side to the other, around the microphone. It is noted that the microphone element can be located anywhere within the back volume that can allow it to perceive pressure variations, or otherwise detect sound, etc.

However, in some embodiments, some leakage between the front volume and the back volume can occur in response to barometric changes in which increased pressure on the external surface of the diaphragm 52 causes the diaphragm 52 to deflect inward, thus increasing pressure in the front volume, and ultimately forcing gas from the front volume to the back volume. This can happen because, in some embodiments, there are one or more pinhole(s) in the diaphragm 54 (sometimes by design), or because the seal around the diaphragm or other components establishing the boundary between the front volume and the back volume is not perfectly sealed or otherwise prone to leaks. To be clear, in at least some exemplary embodiments, such as those where the transducer microphone element assembly 97 is an off-the-shelf component, such as with respect to utilizing a MQM 31692 Knowles microphone as element 97, available from the Knowles microphone company, and there is no perfect seal between what is the back volume of that microphone and the outside of that microphone (a part of which becomes the front volume). Regardless of the physical phenomenon that permits the flow of gas from the front volume to the back volume, such results in a change in the acoustic properties of the microphone. Some embodiments detailed herein address this change in the acoustic properties of the microphone to compensate for such to maintain the microphone performance at the baseline acoustic property or otherwise to relieve the static deflection on the diaphragm to achieve consistent performance. In this regard, at least some of the embodiments detailed herein counteract (including eliminate) this undesirable change of acoustic properties in response to barometric changes, while maintaining and/or improving sensitivity and signal-to-noise ratio.

Figure 15:
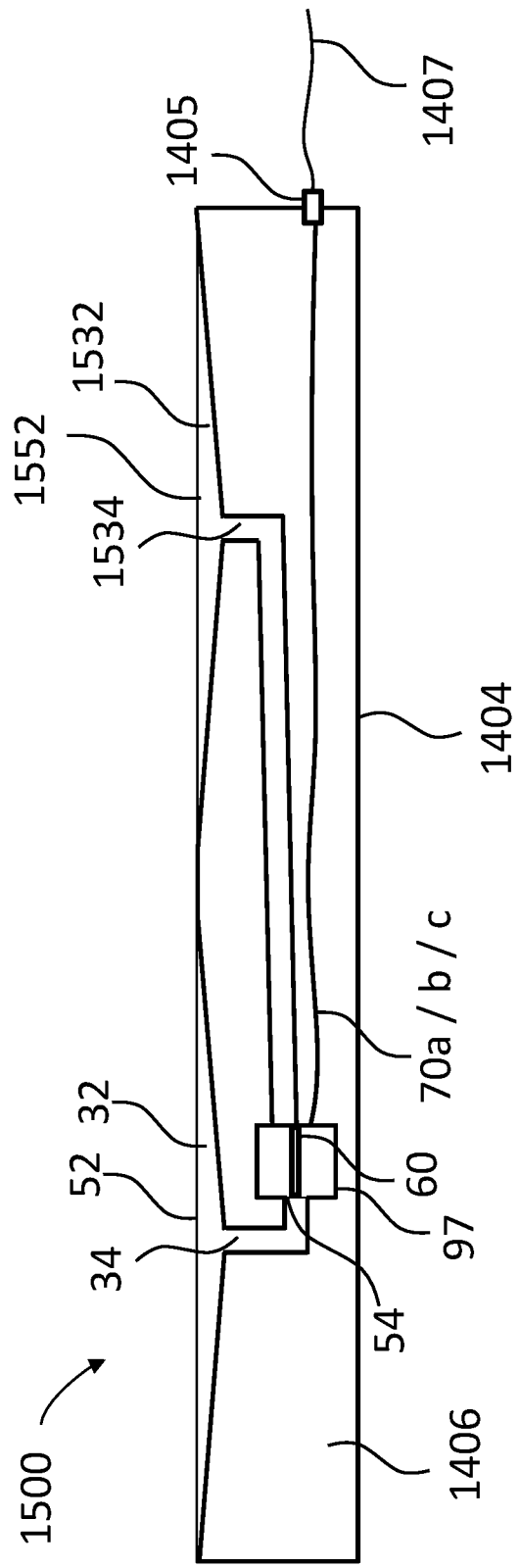
FIGS. 15-19 depicts some exemplary embodiments in which some teachings herein can be utilized.

FIG. 15 presents an exemplary implantable microphone unit 1500 that is configured to be removably attached to another unit implanted in a recipient, such as the unit that includes a signal processor, via electrical lead 1407. This microphone unit can correspond to microphone 12 above. In this embodiment, there is a second diaphragm 1552 that is exposed to the ambient environment (the diaphragm 52 being the first diaphragm exposed to the ambient environment) that extends over a first chamber 1532 that leads to a second chamber 1534. In an exemplary embodiment, at least components 1552 and 1532 are similar to or the same as components 52, 32, respectively, in some or all aspects. The interface between chamber 1534 and 1532 and the initial portion of chamber 1534 can also be the same as the interface of chamber 34 with chamber 32 and the initial portion of chamber 34. That said, in an alternate embodiment, diaphragm 1552, chamber 1532 and/or chamber 1534 can be different in at least some respects than the comparable components of microphone 1400. In an exemplary embodiment, the diaphragm 1552 can be stiffer than the diaphragm 52, the diameter of the chamber 1534, at least before it dog legs towards the transducer microphone element assembly 97, can be larger or smaller than the diameter of the chamber 34, the volume of chamber 1532 can be larger than that of chamber 32 (e.g., by 1.25, 1.5, 1.75, 2.0, 2.25, 2.5, 3, 3.25, 3.5, 4, 5, 6, 7, 8, 9, or 10 times or more). Moreover, while the chamber 32 is funnel-shaped, the chamber 1532 can be of a different shape, such as a wide cylindrical shape. Indeed, in some embodiments, the chamber 1532 can have a rectangular cross-section lying on a plane that is normal to the frame of reference of FIG. 15 and extending in the horizontal direction. Any arrangement or configuration of elements 1552, 1534, and 1532 that can enable the teachings detailed herein can be utilized in at least some exemplary embodiments.

It is noted that with respect to the second diagram 1552, the diaphragm 1552 may not be a diaphragm that is acoustically active or otherwise acoustically sensitive. In an exemplary embodiment, the second diaphragm 1552 is at least 50, 55, 60, 65, 70, 80, 90, 100, 125, 150, 175, 200, 225, 250, 275, 300, 350, 400, 450, 500, 550, 600, 650, 700, 800, 900, 1000, 1100, 1200, 1300, 1400, 1500 or more less acoustically sensitive than the diaphragm 52.

In at least some exemplary embodiments of the embodiment of microphone 1500, any change in barometric pressure that changes the static deflection of diaphragm 52 will also change the static deflection of diaphragm 1552. In at least some exemplary embodiments, this will be results in a pressure change in the back volume (the volume that includes chambers 1532 and 1534) that is similar to and/or the same as the pressure change that occurs in the front volume (the volume that includes chambers 32 and 34). In an exemplary embodiment, this will mitigate (reduce and/or eliminate) any differences in pressure between the front volume and back volume that will have the above noted effects on the acoustic property of the microphone.

Thus, in view of FIG. 15, it can be seen that in an exemplary embodiment, there is an implantable microphone 1500, including a transducer (the transducer microphone element assembly 97 or subcomponents thereof corresponding to a transducer, and a chamber in which a gas is located such that vibrations originating external to the microphone based on sound are effectively transmitted therethrough. In FIG. 15, this chamber is established by chambers 32 and 34. In the embodiment of FIG. 15, the transducer is in effective vibration communication with the chamber (e.g., via diaphragm 54) and the transducer is configured to convert the vibrations traveling via the gas to an electrical signal (which the signal outputted out the feedthrough 1405 is based on (the same signal or a signal that is modified or otherwise generated as a result of the electric signal generated by the transducer microphone element assembly 97)).

In this embodiment, the chamber and the transducer correspond to a microphone system, wherein the chamber corresponds to a front volume of the microphone system, and the transducer includes a back volume corresponding to the back volume of the microphone system, again, as is detailed above. It is noted that the back volume 1534 is contiguous with the inside of the transducer microphone element assembly 97 (which established part of the back volume, in combination with back volume 1534 and 1532). In this embodiment, the implantable microphone is configured to enable pressure adjustment of the front and/or back volume in real time (here, the back volume can be adjusted as a result of deflection of the membrane 1552). By "real time," it is meant a temporal period that is shorter than that which results from natural leakage between the front volume in the back volume, such as the leakage through the pinhole(s) in the diaphragm 54 where the leakage around the diaphragm 54 or other components thereof. In an exemplary embodiment, the pressure adjustment of the front and/or back volume occurs within a time. That is less than 75%, 70%, 65%, 60%, 55%, 50%, 45%, 40%, 35%, 30%, 25%, 20%, 19, 18, 17, 16, 15, 14, 13, 12, 11, 10, 9, 8, 7, 6, 5, 4, 3, 2, or 1% of that which would occur due to normal leaking, if such is present. (It is noted that not all of these values are "real time" values.) In this regard, it can be seen that in an exemplary embodiment, the implantable microphone is configured to adjust a pressure of the front and/or back volume beyond that which results from tolerance leakage therebetween (tolerance leakage being the leakage that results from the fact that the components all have manufacturing tolerances associated therewith and any assembly of components will never be perfect). Put another way, the pressure adjustment that is addressed by the teachings detailed herein is pressure adjustment that is beyond that which results from the mere assembly of the transducer microphone element assembly to the front volume.

In an exemplary embodiment, the pressure adjustment is a pressure adjustment that is achieved based primarily on factors associated with non-transfer of gas from the front volume to the back volume and/or visa-versa. In this regard, because tolerance leaking exists, there are at least some instances where the pressure adjustment is in part due to the leakage, however small that part may be. In an exemplary embodiment, less than 30%, 25%, 20%, 19, 18, 17, 16, 15, 14, 13, 12, 11, 10, 9, 8, 7, 6, 5, 4, 3, 2 or 1% of the resulting pressure adjustment is achieved due to the phenomenon of the gas transfer from the front volume to the back volume or vice versa. In an exemplary embodiment, at least 50%, 55%, 60%, 65%, 70%, 75%, 80%, 85%, 86, 87, 88, 89, 90, 91, 92, 93, 94, 95, 96, 97, 98 or 99% of the pressure adjustment is a result of a change in the volume of the back volume not including any movement of the diaphragm 54, and in some embodiments, the aforementioned percentages are achieved via movement of the diaphragm 1552. Thus, as can be seen, in some embodiments, the implantable microphone is configured to adjust a pressure of the front and/or back volume beyond that which results from leakage associated with the transducer. Still further, in at least some exemplary embodiments, the implantable microphone is configured to adjust a pressure of the front and/or back volume beyond that which results from leakage through a dedicated diaphragm of the transducer and movement of the dedicated diaphragm of the transducer, where "dedicated diaphragm" is the diaphragm 54, as opposed to the diaphragms 52 and 1552, which are not dedicated to the transducer but instead dedicated to the overall implantable microphone. Again, it is noted that diaphragms 52 and 1552 are diaphragms that establish a hermetic barrier between the interior of the implantable microphone and an exterior thereof, as opposed to diaphragm 54, which is completely entirely inside the implantable microphone and not exposed to the ambient environment thereof.

In view of the above, it can be seen that the implantable microphone is configured to enable a volumetric size change of the back volume at a location outside of the transducer (i.e., outside of the transducer microphone element assembly 97). That is, the back volume is established by the volumes of the transducer microphone element assembly 97, the chamber 1632 and the chamber 1634, and in this embodiment, the volume of the back volume is changed outside the transducer microphone element assembly 97. That said, in some embodiments, the size of the back volume can be changed anywhere (e.g., the piston 1620 can travel into and out of the volume established by transducer microphone element assembly 97).

Figure 16:
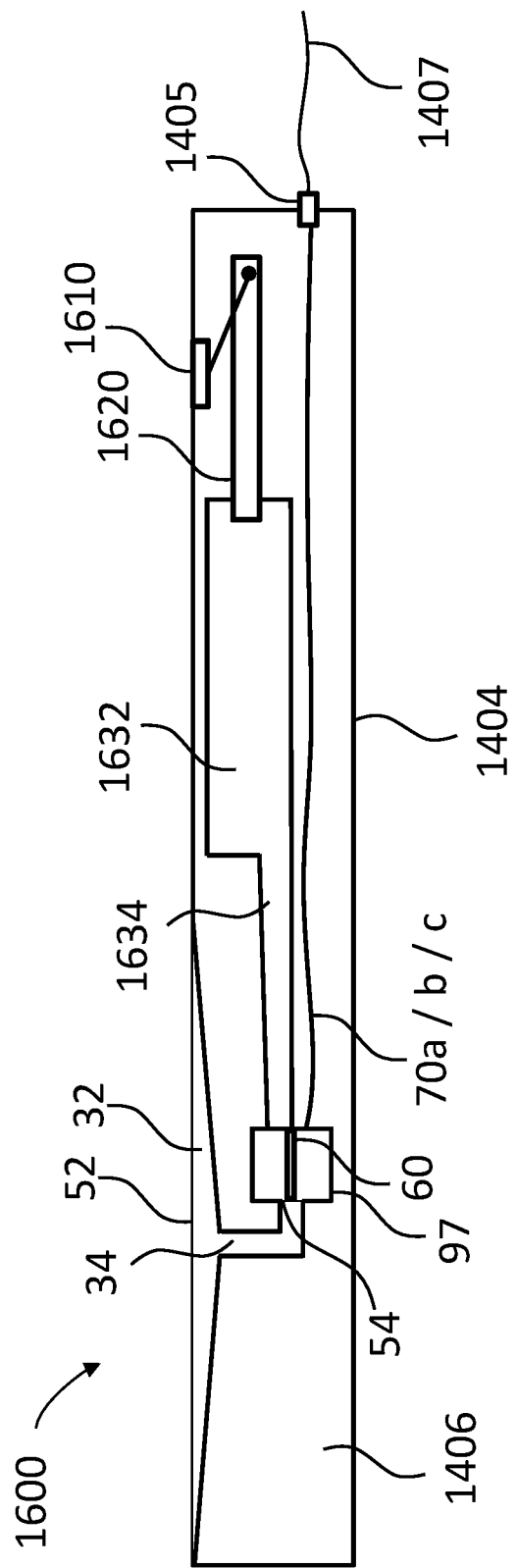
Figure 17:
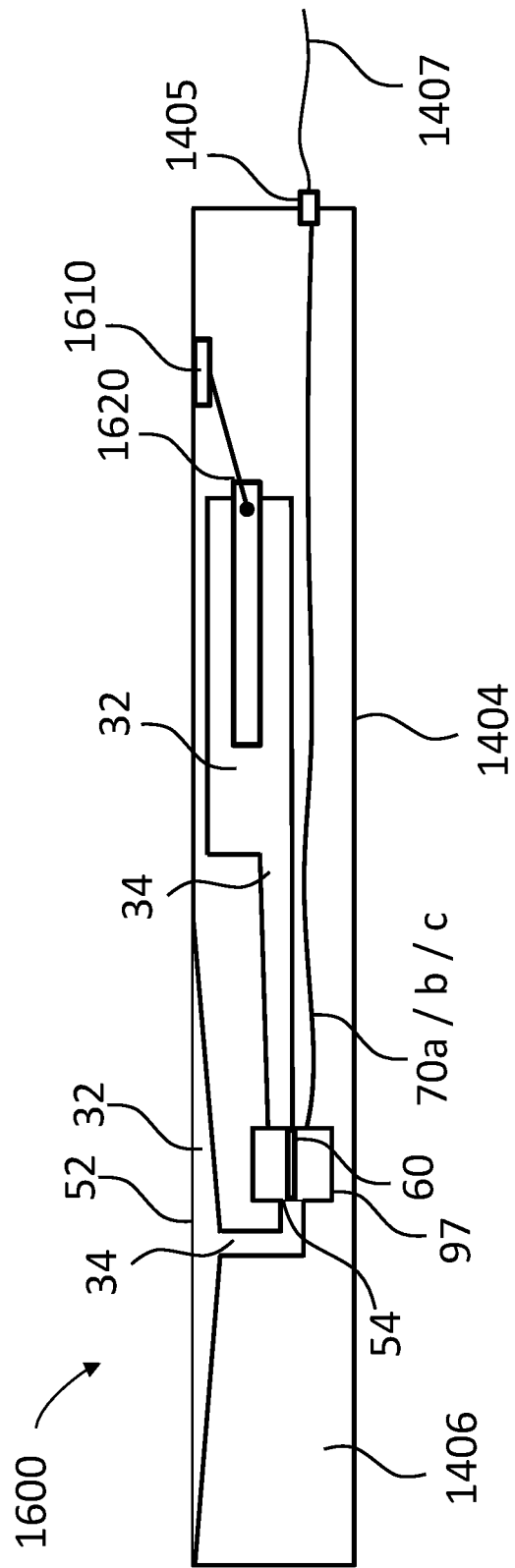

FIG. 16 depicts another exemplary embodiment of an implantable microphone that is configured to enable a volumetric size change of the back volume at a location outside of the transducer. More particularly, FIG. 16 presents the implantable microphone 1600, where the back volume is established by a chamber 1632 and 1634. Unlike chamber 1532 of the embodiment of FIG. 15, chamber 1632 is not bounded by a diaphragm that is exposed to the ambient environment of the implantable microphone 1600. Instead, chamber 1632 is established by solid walls that generally do not deflect (at least not enough to influence the pressure inside the back volume in a meaningful way). Instead, chamber 1632 includes an opening through which piston 1620 can extend and retract. More particularly, piston 1620 is connected to actuator 1610 which is configured to insert and retract piston 1620 when controlled by the implantable microphone or another component so as to adjust the pressure in the back volume to account for a change in pressure of the front volume such as the change in pressure that results from a change in barometric pressure. FIG. 16 depicts the piston 1620 in a retracted state, while FIG. 17 depicts the piston 1620 and an extended state, where the actuator 1610 has actuated to insert the piston 1620 into the chamber 1632. It is to be understood that the actuator 1610 is configured to locate the piston 1620 at various degrees of insertion into the chamber 1632 to obtain various pressure changes in chamber 1632, and thus the back volume. A seal extends about the piston 1620 and is located between the piston 1620 and the walls of the chamber 1632 to establish an airtight seal.

In an exemplary embodiment, a control unit, such as a microprocessor or dedicated computer chip or the like that is part of the implantable microphone or part of the implantable component of the prosthesis, controls actuator 1610 to move the piston 1620. In an exemplary embodiment, the control unit can be control unit 440 detailed above. In an exemplary embodiment, a pressure sensor or the like is located in the front volume and configured to provide an output signal to the control unit indicative of the pressure in the front volume. In an exemplary embodiment, the control unit is configured to evaluate the signal and determine the amount of actuation of actuator 1610 that should be generated to adjust the location of the piston 1620 relative to the chamber 1632 to adjust the pressure in the back volume. In an exemplary embodiment, the control unit relies on instantaneous pressure changes as read from the sensor located in the front volume. In an exemplary embodiment, the control unit takes an average of the pressure changes or otherwise applies a statistical analysis technique to the pressure changes to determine how much to actuate the actuator 1610 to achieve the utilitarian pressure change. By utilizing a statistical technique to analyze the pressure changes, such can avoid having a scenario where the pressure management/volume management system of the implantable microphone overreacts to a pressure change that is of short duration and/or reacts to the natural movement of the diaphragm 52 resulting from sound impingement thereon. Any device, system, and/or method that can enable management of the pressure in the back volume can be utilized in at least some exemplary embodiments.

It is briefly noted that while the embodiments detailed above have focused on changing the volume of the back volume, some embodiments can be directed to changing the volume of the front volume. By way of example only and not by way of limitation, the actuator/piston arrangement of FIG. 16 can be utilized with the chamber 32 of the front volume. In this regard, in an exemplary scenario where the barometric pressure increases, resulting in, or more accurately, what would result, in the absence of the pressure/volume management systems herein, a statically tensioned diaphragm 52 bowing into chamber 32 beyond that which would normally be the case when the pressure of the front volume was balanced with the pressure of the ambient environment of the implantable microphone, the control unit could control the actuator to insert the piston further into chamber 32, thereby decreasing the volume of chamber 32/increasing the pressure inside chamber 32, and preventing the diaphragm 52 from bowing inward and having the static tension that results there from, or otherwise pushing the diaphragm 32 outward to its neutral position and alleviating the static tension that results therefrom.

In view of the above, it can be seen that in an exemplary embodiment, there is an implantable microphone that includes a transducer and a chamber in which a gas is located such that vibrations originating external to the microphone based on sound are effectively transmitted therethrough. In this embodiment, the transducer is in effective vibration communication with the gas, and the transducer is configured to convert the vibrations traveling via the gas to an electrical signal, all consistent with the above embodiments. Still further, the chamber and the transducer correspond to a microphone system, wherein the chamber corresponds to a front volume of the microphone system, and the transducer includes a back volume corresponding to the back volume of the microphone system, and the implantable microphone is configured to enable a volumetric size change of the back volume outside of the transducer and/or the front volume outside the transducer.

Moreover, it is noted that in some exemplary embodiments, the same piston can be utilized to adjust the volume of the back volume and the volume of the front volume. By way of example only and not by way of limitation, the piston can extend into the back volume and into the front volume, where retraction from the back volume will increase extension into the front volume, and vice versa. Still further, in some exemplary embodiments, two separate pistons can be linked together such that movement of one results in movement of the other, and thus the same actuator can be utilized. That said, in some alternate embodiments, two separate pistons in two separate actuators are utilized.

In view of the above, it can be understood that in an exemplary embodiment, the device comprising the implantable microphone can include a piston that moves in a reciprocating manner to change the volumetric size of the back volume and/or the front volume.

It is briefly noted that in at least some exemplary embodiments, the device comprising the implantable microphone that utilizes the diaphragm exposed to an ambient environment (e.g. diaphragm 1552) that moves upon changes in a pressure of the ambient environment changes the volumetric size of the back volume. Of course, with respect to the embodiment of FIG. 15, the device that comprises the implantable microphone includes a second diaphragm exposed to an ambient environment that moves upon receipt of vibrations from the ambient environment based on sound that results in the vibrations so as to transfer those vibrations into the front volume of the implantable microphone to cause the transducer to transduce the vibrations into the output signal indicative of sound. This as opposed to the diaphragm 1552, which does not do so. In this regard, the diaphragm 1552 can be a thicker/less resilient diaphragm than diaphragm 52. In an exemplary embodiment, with respect to the vibrational energy transferred from the outside to the inside by diaphragm 52, diaphragm 1552 transfers less than 75%, 70%, 65%, 60%, 55%, 50%, 45%, 40%, 35%, 30%, 25%, 20%, 19, 18, 17, 16, 15, 14, 13, 12, 11, 10, 9, 8, 7, 6, 5, 4, 3, 2 or 1% of the energy transferred by diaphragm 52. In an exemplary embodiment, this can be achieved by a diaphragm 1552 that is tensioned more than the diaphragm 52, a diaphragm that is stiffer than diaphragm 52, etc. In an exemplary embodiment, diaphragm 1552 is at least 1.25, 1.5, 1.75, 2, 2.25, 2.5, 2.75, 3, 3.5, 4, 4.5, 5, 5.5, 6, 6.5, 7, 7.5, 8, 8.5, 9, 9.5 or 10 times stiffer or thicker, etc., than diaphragm 52. In an exemplary embodiment, diaphragm 52 and diaphragm 1552 are made up of the same materials and/or have the same mechanical properties on a per unit basis (e.g., the thickness of the diaphragm is the driving factor as to how much vibrational energy transfers into the back volume or the front volume).

That said, in an alternate embodiment, the diaphragm 1552 can be the same as the diaphragm 52 or otherwise similar thereto, and other components can be utilized to dampen or otherwise prevent the vibrations that are transferred from reaching the portion of the back volume proximate the transducer microphone element assembly 97 and/or reaching the microphone element 60. By way of example only and not by way of limitation, bellows and the like can be located in chamber 1532 and/or in chamber 1534. A dampening material can be located in the back volume. A vibration canceller can be used to cancel those vibrations. Any device, system and/or method that can enable the management of vibrations associated with the back volume that can have a deleterious effect on the performance of the transducer microphone element assembly can be utilized in at least some exemplary embodiments.

In any event, in at least some embodiments, the device that comprises an implantable microphone includes a first diaphragm (e.g., diaphragm 52) exposed to an ambient environment (e.g., body tissue and/or body fluids) that vibrates in response to ambient sound (e.g., music, voice, etc., all impinging upon skin of the recipient over the first diaphragm) so as to transmit the vibrations based on sound originating external to the microphone to the gas of the front volume. The device also includes a second diaphragm 1552 that is exposed to an ambient environment that moves upon changes in a pressure of the ambient environment to change the volumetric size of the back volume of the implantable microphone. In this embodiment, the first diaphragm is less compliant than the second diaphragm. In an exemplary embodiment, it is about or at least about 2, 2.25, 2.5, 2.75, 3, 3.5, 4, 4.5, 5, 5.5, 6, 7, 8, 9, 10, 11, 12, 13, 14, 15, 16, 17, 18, 19 or 20 times less compliant (or visa versa—see next sentence) or any value or range of values therebetween in about 0.05 increments. That said, in some embodiments, there can be utilitarian value in having the first and second diaphragms being substantially equal in compliance (including equal), while in other embodiments, there can be utilitarian value in having the second diaphragm being more compliant than the first diaphragm (e.g., such as where the back volume is larger than the front volume, and thus a larger volume change in the back volume may be required to equalize the pressure).

Figure 18:
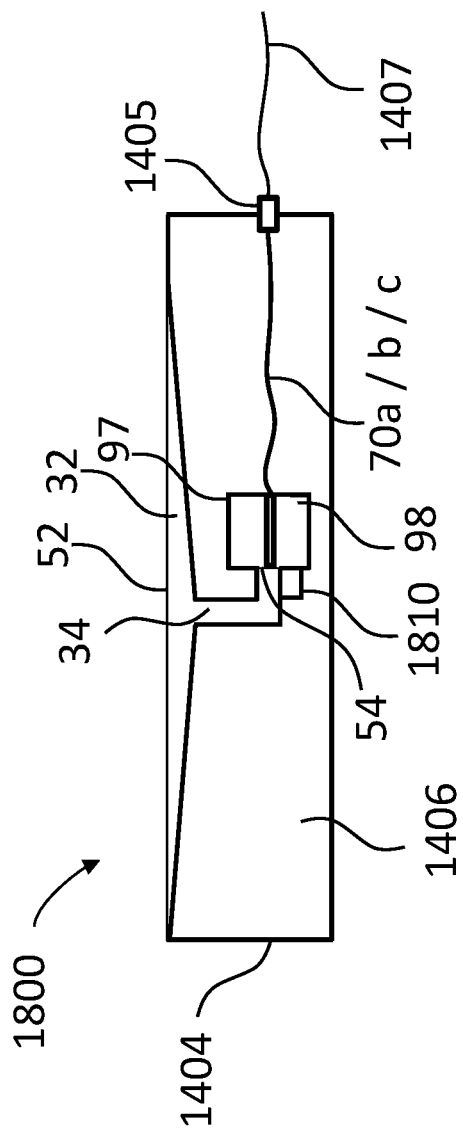

FIG. 18 represents another exemplary embodiment of an implantable microphone, microphone 1800. Here, there is a bypass tube 1810 that extends from the front volume to the back volume in general, and from chamber 34 to the inside of the transducer microphone element assembly 97 (the chamber 98 formed by the walls of the transducer microphone element assembly 97). In an exemplary embodiment, this can have utilitarian value with respect to balancing or otherwise equalizing the pressure between the front volume and the back volume in the event of a pressure imbalance between the two volumes. In an exemplary embodiment, bypass tube 1810 bypasses the diaphragm 54 of the transducer microphone element assembly 97 as can be seen. In an exemplary embodiment, inside of bypass tube 1810 is sized and dimensioned so as to result in a pressure balance between the front and back volume within a timeframe quicker than that which results from normal leakage between the front volume in the back volume. In an exemplary embodiment, the pressure balance between the front and back volume owing to the bypass tube 1810 is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 times or more faster than that which would exist without such (e.g., due to normal leakage/tolerance leakage), all other things being equal. In an exemplary embodiment, bypass tube 1810 can have bellows and the like so as to dampen or otherwise mitigate any pressure variations that result from the movement of diaphragm 52 owing to sound impingement there on. That is, in an exemplary embodiment, bypass tube 1810 can be configured so as to reduce (including eliminate) any effects of sound that could result in a reduction in the sensitivity or otherwise performance of the transducer microphone element assembly 97 (e.g., the bypass tube 1810 providing a conduit for vibrations transmitted through the gas in the front volume to the back volume which impacts the movement of diaphragm 54 in a deleterious manner).

Figure 19:
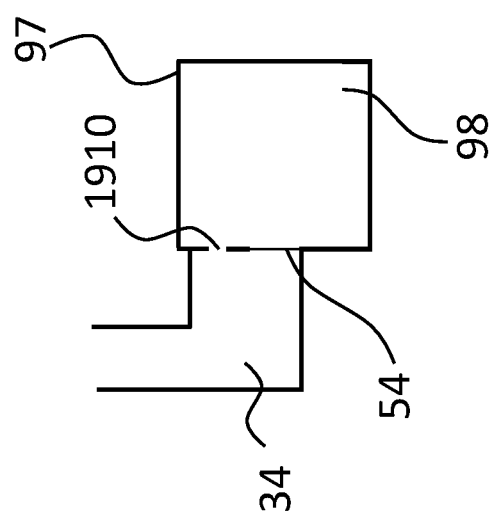

FIG. 19 depicts another exemplary embodiment that can have utilitarian value with respect to pressure equalization, where an orifice 1910 is located in the walls of the transducer microphone element assembly, so as to provide a bypass between the front volume in general, and chamber 34 in particular, around the diaphragm 54, to the back volume in general, and chamber 98 particular. In an exemplary embodiment, orifice 1910 functions in a manner similar to (including the same as) bypass tube 1810 detailed above. In an exemplary embodiment, the diameter of the orifice 1910 is about 10 microns. In an exemplary embodiment, the orifice is any of the following values: about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 microns or any value or range of values therebetween in 0.05 micron increments (e.g., about 11.1, about 20.05, about 8.25 to about 32.20 microns, etc.). In some embodiments, the values can be bigger, such as any value or range of values between 40, 45, 50, 55, 60, 65, 70, 75, 80, 85, 90, 95, 100, 110, 120, 130, 140, 150, 160, 170, 180, 190 or 200 microns in 0.05 micron increments. Any size that can have utilitarian value with respect to practicing the teachings detailed herein can be utilized in at least some embodiments. In an exemplary embodiment, the orifice has a diameter that is at least about 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 times or more the diameter of the pinhole in the diaphragm 54.

Accordingly, in view of the above, in an exemplary embodiment, there is a bypass (e.g., the bypass tube 1810, the orifice 1910, or any other arrangement that can enable the teachings detailed herein) located between the front volume and the back volume that places the front volume into fluid communication with the back volume, bypassing the dedicated diaphragm of the transducer.

Also, in at least some exemplary embodiments, with respect to the bypass, the front volume, the back volume, and the bypass are sized and dimensioned to equalize a pressure imbalance between the front volume and back volume of Z percent relative to the back volume to less than 20, 19, 18, 17, 16, 15, 14, 13, 12, 11, 10, 9, 8, 7, 6, 5, 4, 3, 2 or 1% of the maximum pressure imbalance within H seconds from the maximum pressure imbalance. In an exemplary embodiment, Z is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190 or 200 or more, and H is 2, 3, 4, 5, 6, 7, 8, 9, 10, 11, 12, 13, 14, 15, 16, 17, 18, 19, 20, 21, 22, 23, 24, 25, 26, 27, 28, 29 or 30. By relative to the back volume, it is meant that the back volume is the denominator. Thus, a pressure of 2.2 units in the front volume and a pressure of 2.0 units in the back volume would be a 10% pressure difference relative to the back volume. The 2.2 units, if the maximum pressure imbalance, is the time from which H starts (i.e., as opposed to 2.15 units). In this regard, the above features are linked to a percentage of the largest pressure imbalance, as opposed to the elimination completely of the pressure imbalance.

Also, in an exemplary embodiment, the front volume, the back volume and the bypass is sized and dimensioned to prevent the pressure imbalance of Z percent to be equalized faster than I seconds where, in an exemplary embodiment, I is 0.001, 0.002, 0.003, 0.004, 0.005, 0.006, 0.007, 0.008, 0.009. 0.10, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.40, 0.45, 0.5, 0.55, 0.6, 0.65, 0.7, 0.75, 0.8, 0.85, 0.9, 1, 1.25, 1.5, 1.75 or 2.

It is noted that while the above performance values have been provided in terms of the bypass of the embodiments of FIGS. 18 and 19, these performance values can also be applicable to the other pressure management features detailed herein and variations thereof. Accordingly, in an exemplary embodiment, such as with reference to the embodiments of FIGS. 15 and 16, there is a device that is configured to change the volumetric size of the back volume (and/or front volume) to equalize a pressure imbalance between the front volume and back volume of Z percent relative to the back volume no faster than I seconds. Also, in an exemplary embodiment, the device is configured to change the volumetric size of the back volume (and/or front volume) to equalize a pressure imbalance between the front volume in the back volume of Z percent relative to the back volume within H seconds.

Figure 20:
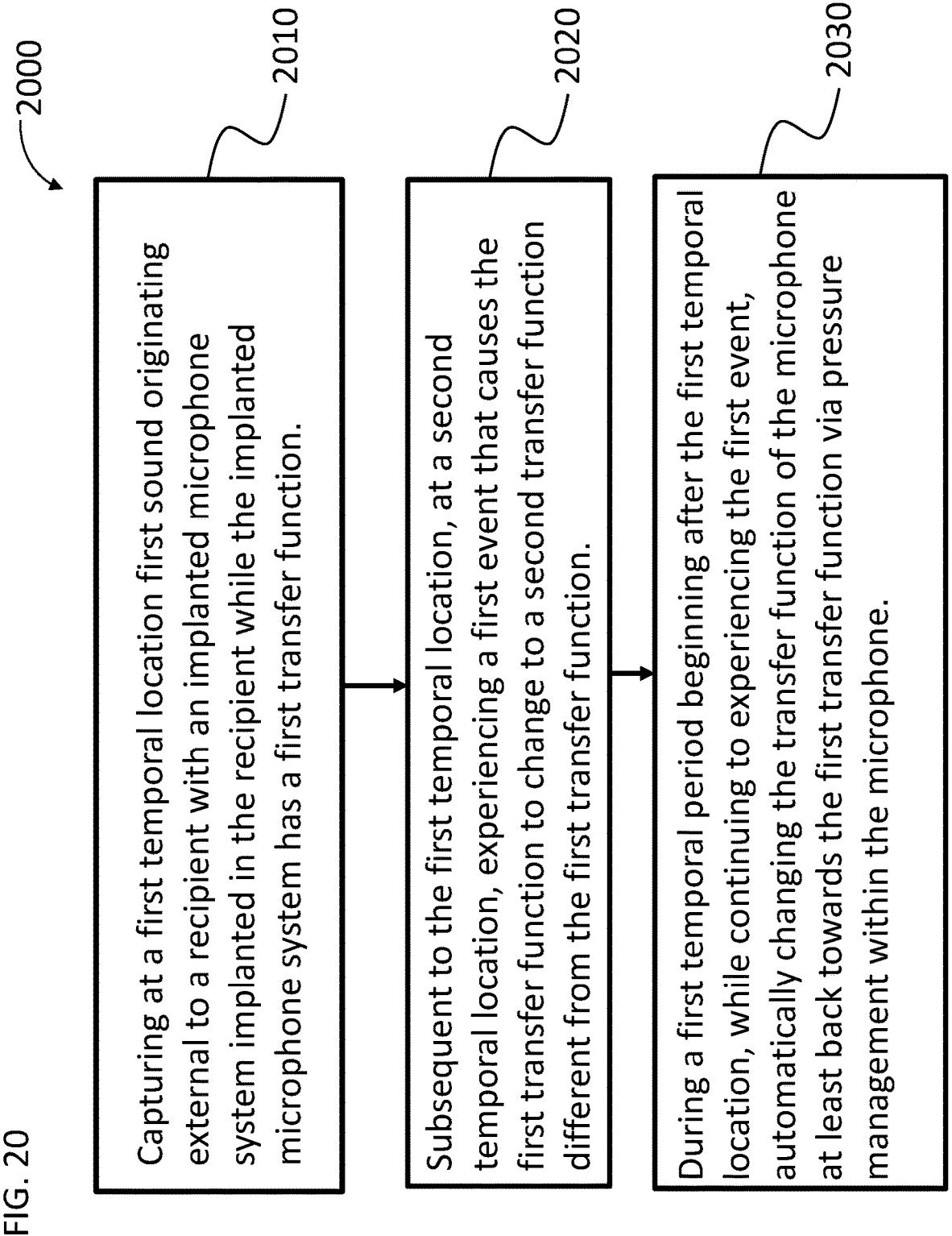
FIG. 20 depicts an exemplary flowchart according to an exemplary embodiment.

In view of the above, it is to be understood that the teachings above can enable a method of managing pressure within a microphone. In this regard, for example, FIG. 20 presents an exemplary algorithm for an exemplary method, method 2000, that includes method action 2010, which includes capturing at a first temporal location first sound originating external to a recipient with an implanted microphone system implanted in the recipient while the implanted microphone system has a first transfer function. By way of example only and not by way of limitation, this can correspond to a transfer function of the implanted microphone system that corresponds to a balanced pressure in the front volume and the back volume (e.g., a pressure of 5 units in the front volume and a pressure of 5 units in the back volume). Method 2000 also includes method action 2020, which includes, subsequent to the first temporal location, at a second temporal location, experiencing a first event that causes the first transfer function to change to a second transfer function different from the first transfer function. In an exemplary embodiment, this second temporal location can be a location 3 minutes after the first temporal location, and the event can be, for example, the pressurization of a commercial aircraft which reduces the ambient pressure by a certain amount. In an exemplary embodiment, the transfer function is a function of pressure imbalance. In such an exemplary scenario, the ambient pressure on the skin of the recipient would thus be reduced, and the diaphragm 52 could bow outward away from the front volume, and thus reduce the pressure in the front volume (e.g., a pressure of 4.8 units in the front volume in a pressure of 5 units in the back volume). Thus, a pressure imbalance between the front volume and the back volume would exist, which would change the transfer function of the microphone system from the first transfer function to the second transfer function. Method 2000 further includes method action 2030, which includes during a first temporal period beginning after the first temporal location (e.g., such as a period beginning at or after the second temporal location), while continuing to experiencing the first event, automatically changing the transfer function of the microphone system at least back towards the first transfer function via pressure management within the microphone. In an exemplary embodiment, this can include, for example, the utilization of the piston arrangement of the embodiment of FIG. 16, or the diaphragm exposed to the environment of the embodiment of FIG. 15, etc., Which would adjust while the aircraft is pressurized, and thus adjust during a temporal period while continuing to experience the first event. In an exemplary embodiment, at least in some instances, upon the equalization of the pressure between the front volume and the back volume, the transfer function of the implantable microphone system would be that which was the case at the first temporal location. In an exemplary embodiment, at least in some instances, upon the equalization of the pressure between the front volume and the back volume and the back volume, the transfer function of the implantable microphone might be different from that which was the case at the first temporal location, but still much closer to that which was the case at the first temporal location than that which would be the case in the absence of the pressure management teachings detailed herein and/or variations thereof.

In some exemplary embodiments, the first event lasts more than at least 10, 15, 20, 25, 30, 35, 40, 45, 50, 55, 60, 75, 90, 105 seconds, 2 minutes, 2.5, 3, 3.5, 4, 4.5, 5, 5.5, 6, 6.5, 7, 7.5, 8, 9, 10, 11, 12, 13, 14, 15, 20, 25, 30, 35, 40, 45, 50, 55 or 60 minutes or more at a steady state. In at least some exemplary embodiments, within a time period about half of any of the aforementioned values (e.g., 5, 7.5, 10, 12.5, 15, 17.5, 20, 22.5, 25 seconds, etc.), while continuing to experience the first event, method 2000 further includes the action of automatically changing the transfer function of the microphone to effectively B % of the way back to the first transfer function via the pressure management within the microphone, where B can be 50, 55, 60, 65, 70, 75, 80, 85, 86, 87, 88, 89, 90, 91, 92, 93, 94, 95, 96, 97, 98, 99 or 100.

In view of the teachings above, it is clear that in some embodiments, the microphone system that is the subject of method 2000 is part of a hearing prosthesis that includes an implanted noise cancellation system, such as any of the noise cancellation systems detailed above or variations thereof. Also consistent with the teachings detailed above, the noise cancellation system includes an algorithm that cancels feedback, which algorithm is at least partially dependent on the transfer function of the microphone and which algorithm accommodates changes in the transfer function of the microphone. In some embodiments associated with the execution of method 2000, the pressure management system has prevented the noise cancellation system from chasing the changes in the transfer function of the microphone between the first temporal location and an end of the first temporal period. Some additional features of such will be described below.

Also, it is noted that the pressure management systems detailed herein and variations thereof can be utilized while the microphone is functioning to capture sound. Accordingly, in an exemplary embodiment of the method 2000, sound is captured during the first temporal period while the pressure is managed. The sound capture causes a diaphragm (e.g., diaphragm 54) of a transducer of the microphone system to vibrate, wherein the pressure management executed during method action 2000 effectively does not impact a vibration characteristic of the diaphragm resulting from the sound (e.g., it does not tension the diaphragm 54 in a manner that impacts the vibration characteristic thereof).

Figure 21:
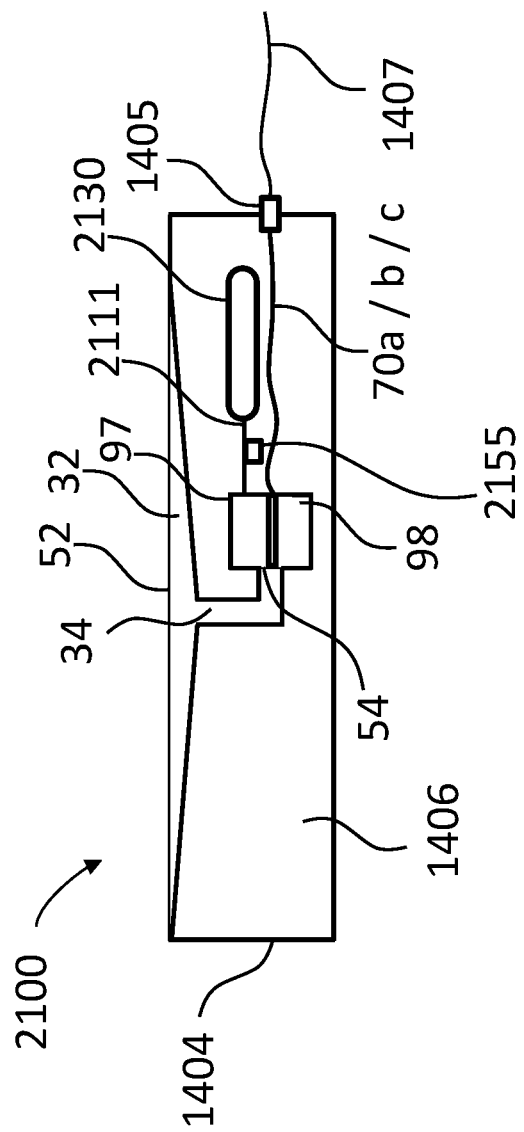
FIG. 21 depicts an exemplary embodiment in which some teachings herein can be utilized.

As noted above, embodiments of method 2000 to be practiced utilizing the piston of the embodiment of FIG. 16. Thus, in an exemplary embodiment, the pressure management of method 2000 includes actively equalizing pressure in the front volume and the back volume of the transducer of the implanted microphone. FIG. 21 depicts another exemplary embodiment of a microphone 2100 that includes an active pressure management system. As can be seen, a tank of compressed gas 2130 is in fluid communication with the chamber 98 via piping 2111. Pump 2155 is configured to automatically pump gas from tank 2130 or to tank 2130 so as to increase or decrease the pressure in the back volume, and thus in some embodiments, equalize the pressure of the back volume with the front volume.

Of course, some embodiments are such that the pressure management of method 2000 is practiced utilizing passive equalization methods. That is, the press or management of method 2000 includes passively equalizing pressure in a front volume and a back volume of the transducer of the implanted microphone system. By way of example only and not by way of limitation, the utilization of the orifice of the embodiment of FIG. 19 is such an exemplary embodiment.

Figure 22:
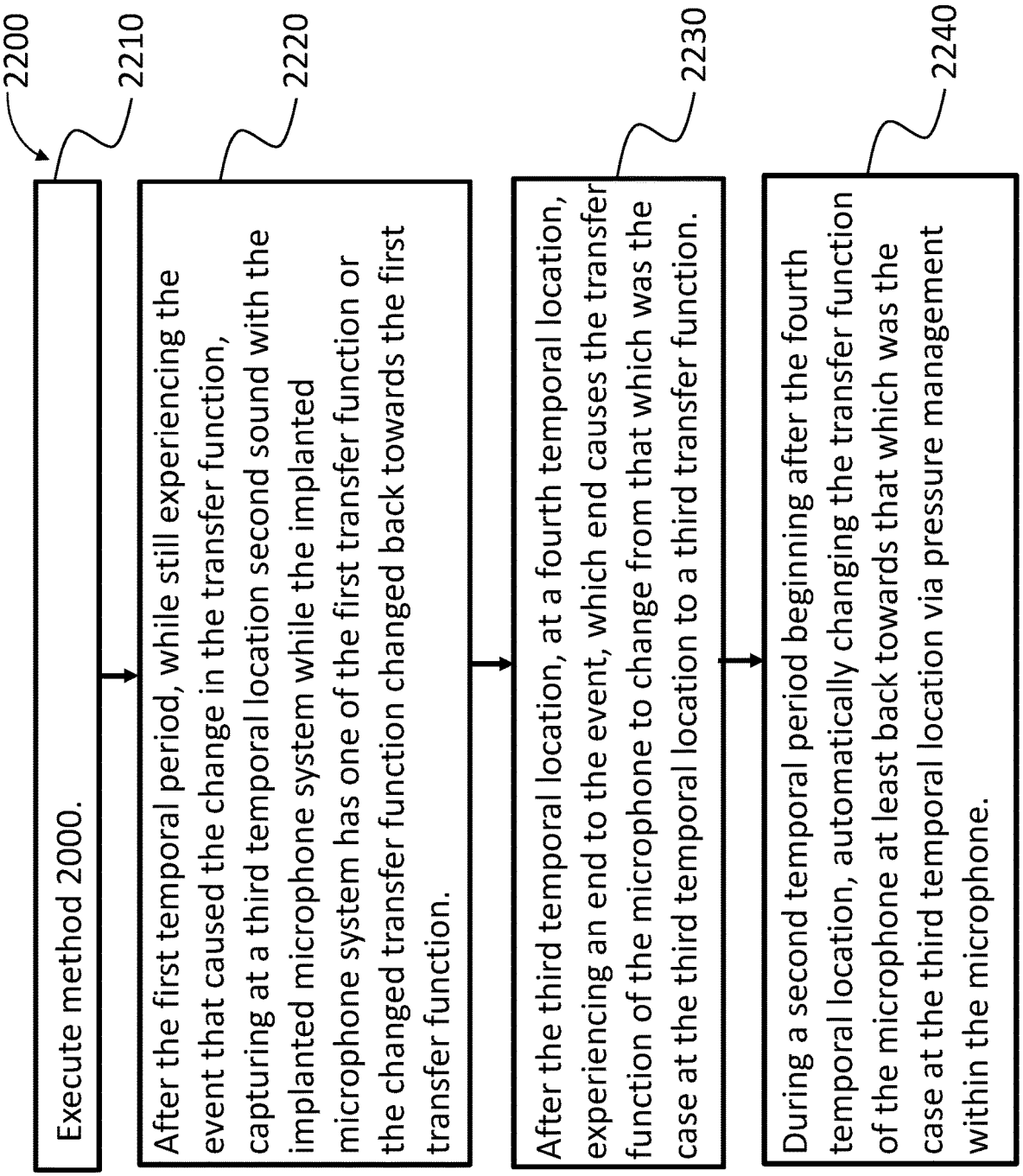
FIG. 22 depicts an exemplary flowchart according to an exemplary embodiment.

FIG. 22 presents a flowchart for another exemplary method, method 2200. Method 2200 includes method action 2210, which includes executing method 2000. Method 2000 further includes method action 2220, which includes, after the first temporal period, while still experiencing the event that caused the change in the transfer function, capturing at a third temporal location second sound with the implanted microphone system while the implanted microphone system has one of the first transfer function or the changed transfer function changed back towards the first transfer function. In an exemplary embodiment, the first sound can be the voice of a passenger, for example, sitting to the right of the recipient of the implanted microphone, while the passenger is discussing the results of a baseball game aired the night before television, and the second sound can be the voice of the passenger while the passenger is discussing the news coverage of the baseball game, where the third temporal location is after the plane is taken off, where is the first temporal location is while the plane was sitting on the tarmac prior to the cabin doors of the aircraft being shut and sealed and the aircraft pressurization system being activated. Method 2200 further includes method action 2230, which includes, after the third temporal location, at a fourth temporal location, experiencing an end to the event, which end causes the transfer function of the microphone to change from that which was the case at the third temporal location to a third transfer function. By way of example only and not by way of limitation, the fourth temporal location can be at a point where the aircraft has landed. In an exemplary embodiment, the aircraft took off from a city located substantially at sea level, such as, for example, Washington, D.C. Reagan National Airport, and landed, for example, at Denver Airport in Denver, Colo., which is about a mile above sea level, and thus has an ambient pressure that is different than that from Washington, D.C. And thus, the end of the first event of method action 2230 is a result of, for example, the cabin doors opening and the pressurization system of the aircraft being shut down, and thus the pressure within the aircraft changing to that of the pressure at the Denver airport. Method 2200 further includes method action 2240, which includes, during a second temporal period beginning after the fourth temporal location, automatically changing the transfer function of the microphone at least back towards that which was the case at the third temporal location via pressure management within the microphone. In an exemplary embodiment, this can correspond to adjusting the pressure within the microphone system to accommodate the fact that the ambient pressure is now that which corresponds to a mile above sea level as opposed to that which corresponds to 8,000 feet above sea level which is the pressurization of a cabin of an aircraft. Accordingly, it can be understood that in at least some exemplary embodiments, there is utilitarian value with respect to not fully changing the transfer function of the microphone system back to that which was the case at the beginning of the first event.

Figure 23:
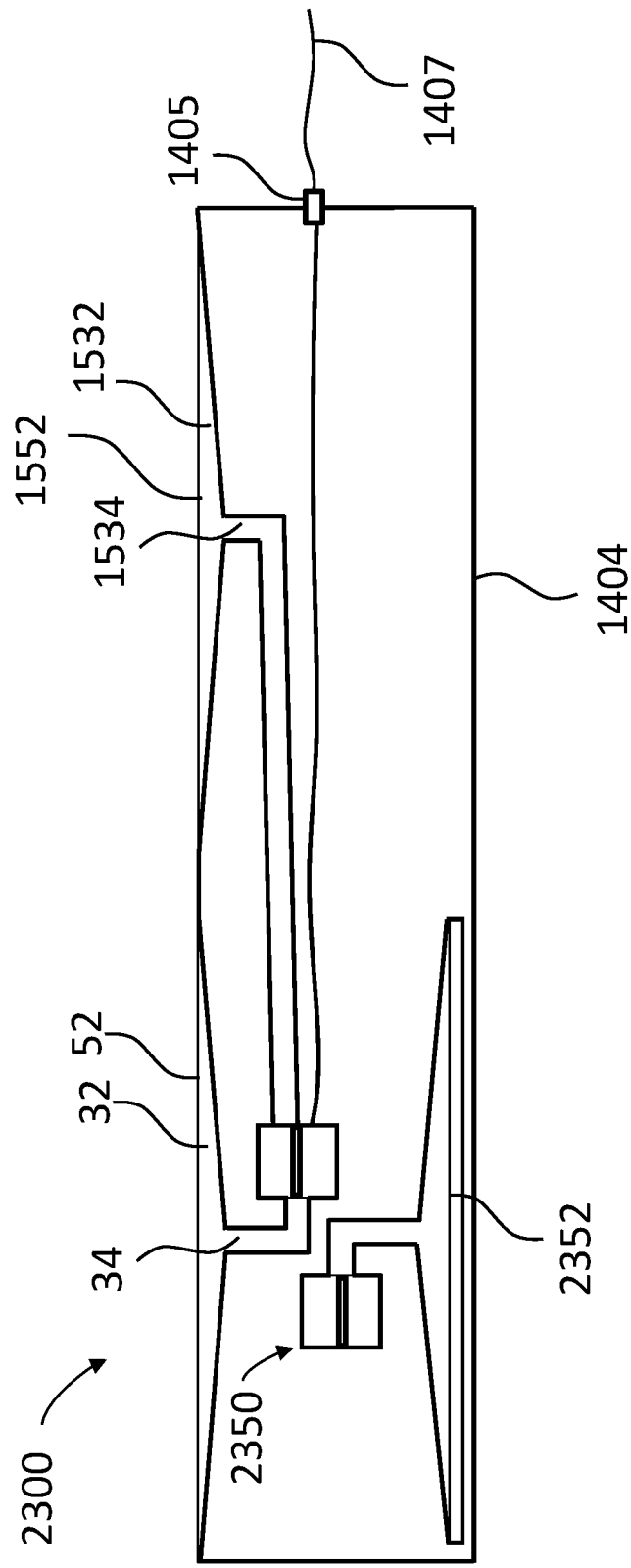
FIG. 23 depicts an exemplary embodiment in which some teachings herein can be utilized.

As noted above, embodiments of the teachings herein can correspond to a hearing prosthesis, comprising, an implantable microphone system, and an implantable noise cancellation system (or, as some may describe, a sound capture sub-system of an implantable microphone system, and a noise cancellation system of the implantable microphone system, depending on the terminology one uses). FIG. 23 depicts an exemplary embodiment of such an implantable microphone system 2300. In this embodiment, microphone 2300 corresponds to microphone 1500 detailed above, but with the addition of a noise cancellation system 2350 (which can correspond to the accelerometer/motion sensor 71 detailed above). In an exemplary embodiment, noise cancellation system 2350 corresponds to any of the noise cancellation systems detailed above and/or variations thereof. It is noted that microphone 2300 can correspond to microphone 12/412 above and motion sensor 71/accelerometer 470 detailed above, as a single unit (i.e., can correspond to transducer system 480). As can be seen, noise cancellation system 2350 includes components that generally correspond to the components of the sound capture system. In this regard, the noise cancellation system 2350 includes a front volume that is in fluid communication with a diaphragm 2352, which front volume extends to a transducer microphone element assembly that has a back volume. The transducer microphone element assembly can correspond to that of the sound capture system. A difference between the noise cancellation system and the sound capture system is that the diaphragm 2352 is isolated from sound of the ambient environment, as opposed to the diaphragm 52 of the sound capture system. Accordingly, the diaphragm 2352 vibrates or otherwise moves with vibration/movement of the housing 1404, but not due to sound. Conversely, diaphragm 52 moves or otherwise vibrates as a result of the vibration/movement of the housing 1404, in addition to vibration resulting from sound. Not shown is are the signal lines output from the transducer microphone element assembly of the noise cancellation system which lead to the microphone system so that the noise cancellation system can cancel at least in part of the signal that is outputted from the transducer microphone element assembly of the sound capture system.

In some embodiments of such embodiments, the hearing prosthesis is configured to evoke a hearing percept based on frequencies above a given frequency (e.g., 100 Hz, 60 Hz, etc.) captured by the microphone system and adjust the noise cancellation system transfer function to accommodate for changes in an environment of the recipient (e.g., pressure changes owing to the movement of a weather front, pressure changes owing to the fact that the recipient is swimming, etc.). In some exemplary embodiments, the implantable microphone is configured to adjust a pressure within a microphone volume (e.g., the back volume, the front volume) in a timeframe fast enough that the adjustment accommodates the noise cancellation system and slow enough that the adjustment accommodates the microphone system. Accordingly, in an exemplary embodiment, this can avoid a scenario where the pressure management system "chases" the noise cancellation system.

In some embodiments of this hearing prosthesis, the hearing prosthesis is configured to evoke a hearing percept based on a time constant corresponding to more than P Hz and adjust the noise cancellation system transfer function to accommodate the change in the environment within about V of a minute, where P can be 30, 35, 40, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85, 90, 95 or 100, and V is 0.05, 0.1, 0.15, 0.2, 0.25, 0.3, 0.35, 0.4, 0.45, 0.5, 0.55, 0.6, 0.65, 0.7, 0.75, 0.8, 0.9, 1.0, 1.1, 1.2, 1.3, 1.4 or 1.5. To be clear, about 0.25 of a minute corresponds to about 15 seconds, about 0.5 of a minute corresponds to about a half of a minute, etc.

Based on the above, it can be seen that the implantable microphone system of some embodiments can include a first transducer (e.g., the transducer microphone element assembly of the sound capture system) and a first chamber in which a gas is located such that vibrations originating external to the microphone are effectively transmitted therethrough, wherein the first transducer is in effective vibration communication with the gas, wherein the transducer is configured to convert the vibrations traveling via the gas to a first electrical signal. Further, the first chamber corresponds to a first front volume of the microphone system, and the first transducer includes a first back volume corresponding to the first back volume of the transducer system.

Further, in this exemplary embodiment, the implantable noise cancellation system includes a second transducer (e.g., the transducer microphone element assembly of the noise cancellation system) and a second chamber in which a gas is located such that vibrations originating external to the microphone are effectively transmitted therethrough. Consistent with the above-noted theory of operation of the noise cancellation system, the second chamber is at least substantially isolated from noise vibrations that are captured by the microphone system. The second transducer is in effective vibration communication with the gas of the second chamber, and the second transducer is configured to convert the vibrations traveling via the gas of the second chamber to a second electrical signal. Here, the second chamber corresponds to a second front volume of the noise cancellation system (where "second" is used for naming purposes only, there are not "two" front volumes of the noise cancellation system). In this embodiment, the hearing prosthesis is configured to enable pressure adjustment of the first back volume in real time (e.g., using any of the embodiments detailed herein, whether active or passive).

In some embodiments, the first back volume is fluidically linked to the second back volume such that the pressure adjustment in the first back volume also adjusts the pressure of the second back volume. In some embodiments of such an embodiment, because the second front volume of the noise cancellation system is isolated from the ambient environment of the implantable hearing prostheses such that a pressure change of the ambient environment will not affect the pressure in the front volume, the hearing prosthesis is configured to also change a pressure within the front volume of the noise cancellation system (the second front volume) so as to balance the pressure of the second front volume with the pressure of the second back volume, which pressure has changed owing to the adjustments of the pressure within the first back volume of the implantable microphone system. That is, in an exemplary embodiment, there is a system to manage the pressure between the front volume and the back volume of the noise cancellation system. Such an embodiment can accommodate changes associated with the shared back volume between the microphone system and the noise cancellation system if such is present.

Conversely, in some embodiments, the first back volume is fluidically isolated from the second back volume such that the pressure adjustment in the first back volume does not adjust the pressure of the second back volume.

In some embodiments, the hearing prosthesis is configured such that the pressure adjustment does not impact effective operation of a feedback mitigation algorithm of the hearing prosthesis (i.e., there can be some impact, but the feedback mitigation algorithm is not effectively impacted/ the feedback mitigation algorithm will continue to be effective). In at least some exemplary embodiments of such, this prevents or otherwise mitigates the above-noted phenomenon where the feedback management system chases the transfer function of the microphone. In at least some exemplary embodiments, the results of the feedback mitigation algorithm of the hearing prosthesis of the same as if the pressure management system was not present or otherwise not functional. In an exemplary embodiment, the results of the feedback mitigation algorithm are at least a 70, 75, 80, 85, 90, 91, 92, 93, 94, 95, 96, 97, 98, 99 or 100% reduction in noise relative to that which would be the case in the absence of the operation of the feedback mitigation algorithm when the pressure management system is functioning. In an exemplary embodiment, the time that it takes the feedback mitigation algorithm to converge on a set of filter coefficients to be applied to eliminate/reduce feedback is no more than 75, 70, 65, 60, 55, 50, 45, 40, 35, 30, 25, 24, 23, 22, 21, 20, 19, 18, 17, 16, 15, 14, 13, 12, 11, 10, 9, 8, 7, 6, 5, 4, 3, 2 1 or 0% longer than that which would be the case in the absence of the pressure management system functioning.

It is noted that in some embodiments, the back volume is a zero compliance back volume (e.g., there is no second diaphragm exposed to the ambient environment).

In view of the above, it can be seen that at least some exemplary embodiments are directed towards an implantable microphone that reduces (including eliminates) the barometric change in pressures associated therewith while permitting the acoustic change in pressure to be utilized as a basis to transduce sound into electrical signal.

In an exemplary embodiment, there is a device, comprising: an implantable microphone, including a transducer, and a chamber in which a gas is located such that vibrations originating external to the microphone based on sound are effectively transmitted therethrough, wherein the transducer is in effective vibration communication with the gas, wherein the transducer is configured to convert the vibrations traveling via the gas to an electrical signal, the chamber and the transducer correspond to a microphone system, wherein the chamber corresponds to a front volume of the microphone system, and the transducer includes a back volume corresponding to the back volume of the microphone system, and the implantable microphone is configured to enable pressure adjustment of the front and/or back volume in real time. In an exemplary embodiment of this embodiment, the implantable microphone is configured to enable a volumetric size change of at least one of the back volume outside of the transducer or the front volume outside the transducer.

It is noted that any one or more teachings detailed herein can be combined with any other one or more teachings detailed herein in at least some exemplary embodiments, unless otherwise specifically excluded or unless the art is not enable such. Any disclosure of an apparatus herein or a system herein corresponds to a disclosure of a method of utilizing such. Any disclosure of a method action herein corresponds to a disclosure of a system and/or a device configured to execute such method actions unless otherwise specified or unless the art does not enable such. Any disclosure of a manufacturing operation herein corresponds to a disclosure of an apparatus that results from such manufacturing operation, and any disclosure of an apparatus herein corresponds to a disclosure of a method of making such apparatus. Any device, system, and/or method that can enable the teachings detailed herein to be practiced can be utilized in at least some exemplary embodiments to implement the teachings herein. Any element or action herein can be not present in an exemplary embodiment.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A method, comprising:
capturing at a first temporal location first sound originating external to a recipient with an implanted microphone system implanted in the recipient while the implanted microphone system has a first transfer function;
subsequent to the first temporal location, at a second temporal location, experiencing a first event that causes the first transfer function to change to a second transfer function different from the first transfer function; and
during a first temporal period beginning after the first temporal location, while continuing to experiencing the first event, automatically changing the transfer function of the microphone system at least back towards the first transfer function via pressure management within the implanted microphone system.

2. The method of claim 1, wherein:
the first event last more than 30 seconds at a steady state; and
within about 15 seconds during the 30 seconds, while continuing to experiencing the first event, automatically changing the transfer function of the microphone at least about 80% of the way back to the first transfer function via the pressure management within the microphone.

3. The method of claim 1, wherein:
the first event last more than 30 seconds at a steady state; and
within about 15 seconds during the 30 seconds, while continuing to experiencing the first event, automatically changing the transfer function of the microphone to effectively 100% of the way back to the first transfer function via the pressure management within the microphone.

4. The method of claim 1, wherein:
the microphone system is part of a hearing prosthesis that includes an implanted noise cancellation system;
the noise cancellation system includes an algorithm that cancels feedback, which algorithm is at least partially dependent on the transfer function of the microphone system and which algorithm accommodates changes in the transfer function of the microphone system; and
the pressure management system has prevented the noise cancellation system from chasing the changes in the transfer function of the microphone between the first temporal location and an end of the first temporal period.

5. The method of claim 1, wherein:
sound is captured during the first temporal period while the pressure is managed, the sound capture causing a diaphragm of a transducer of the microphone system to vibrate, wherein the pressure management effectively does not impact a vibration characteristic of the diaphragm resulting from the sound.

6. The method of claim 1, wherein:
the pressure management includes actively equalizing pressure in a front volume and a back volume of a transducer of the implanted microphone system.

7. The method of claim 1, further comprising:
evoking a hearing percept based on output of the implanted microphone system based on the first sound captured by the implanted microphone system.

8. The method of claim 1, further comprising:
during the first temporal period, evoking a hearing perception based on sound captured by the implanted microphone.

9. The method of claim 1, further comprising:
during the first temporal period, while continuing to experience the first event, evoking a hearing percept based on sound captured by the implanted microphone.

10. The method of claim 1, wherein:
the pressure management includes transferring fluid from a front volume to a back volume of the implantable microphone system.

11. The method of claim 1, wherein:
the microphone system is part of a hearing prosthesis that includes a feedback mitigation system, and the pressure management does not impact effective operation of a feedback mitigation algorithm of the feedback mitigation system.

12. The method of claim 1, further comprising:
evoking a hearing percept using the implanted microphone based on a time constant corresponding to more than 60 Hz during the first temporal period while the transfer function is between the first transfer function and the second transfer function.

13. The method of claim 1, wherein:
the microphone system is part of an implantable hearing prosthesis; and
the pressure management adjusts a pressure in a front volume of the implanted microphone system in a timeframe fast enough that the adjustment accommodates a noise cancellation system of the hearing prosthesis and slow enough that the adjustment accommodates the microphone system.

14. The method of claim 1, wherein:
the implantable microphone system is part of a hearing prosthesis that includes an implanted noise cancellation system;
the hearing prosthesis is configured to adjust a transfer function of the noise cancellation system to accommodate for the first event; and
the implantable microphone system is configured to adjust a pressure within a microphone volume via the pressure management of the microphone system in a timeframe fast enough that the adjustment accommodates the noise cancellation system and slow enough that the adjustment accommodates the implantable microphone system.

* * * * *